United States Patent
Wang et al.

(10) Patent No.: US 9,395,281 B2
(45) Date of Patent: Jul. 19, 2016

(54) AEROSOL MOBILITY IMAGING FOR RAPID SIZE DISTRIBUTION MEASUREMENTS

(71) Applicants: Brookhaven Science Associates, LLC, Upton, NY (US); Aerosol Dynamics, Inc., Berkeley, CA (US)

(72) Inventors: Jian Wang, Setauket, NY (US); Susanne Vera Hering, Berkeley, CA (US); Steven Russel Spielman, Berkeley, CA (US); Chongai Kuang, Sound Beach, NY (US)

(73) Assignee: BROOKHAVEN SCIENCE ASSOCIATES, LLC, Upton, NY (US)

( * ) Notice: Subject to any disclaimer, the term of this patent is extended or adjusted under 35 U.S.C. 154(b) by 0 days.

(21) Appl. No.: 14/434,263

(22) PCT Filed: Oct. 8, 2013

(86) PCT No.: PCT/US2013/063885
§ 371 (c)(1),
(2) Date: Apr. 8, 2015

(87) PCT Pub. No.: WO2014/058882
PCT Pub. Date: Apr. 17, 2014

(65) Prior Publication Data
US 2015/0268140 A1    Sep. 24, 2015

Related U.S. Application Data

(60) Provisional application No. 61/710,858, filed on Oct. 8, 2012.

(51) Int. Cl.
*G01N 15/02* (2006.01)
*G01N 1/28* (2006.01)
*G01N 15/06* (2006.01)
*G01N 21/17* (2006.01)
*G01N 33/00* (2006.01)
*G01N 33/18* (2006.01)
*G01N 15/00* (2006.01)

(52) U.S. Cl.
CPC .............. *G01N 1/28* (2013.01); *G01N 15/0227* (2013.01); *G01N 15/0255* (2013.01); *G01N 15/065* (2013.01); *G01N 21/17* (2013.01); *G01N 33/0009* (2013.01); *G01N 33/18* (2013.01); *G01N 2015/0046* (2013.01)

(58) Field of Classification Search
USPC ...................... 356/36–38, 335–336, 437–438; 436/174
See application file for complete search history.

(56) References Cited

U.S. PATENT DOCUMENTS

| | | | |
|---|---|---|---|
| 5,903,338 | A | 5/1999 | Mavliev et al. |
| 7,298,486 | B2 | 11/2007 | Wang et al. |
| 2012/0048112 | A1 | 3/2012 | Hering et al. |

OTHER PUBLICATIONS

International Search Report of International Application No. PCT/US2013/063885—Date Mailed: Dec. 16, 2013, 4 pages.
Written Opinion of the Searching Authority of International Application No. PCT/US2013/0638885—Date Mailed: Dec. 16, 213, 6 pages.

*Primary Examiner* — Tri T Ton
(74) *Attorney, Agent, or Firm* — Hoffmann & Baron, LLP

(57) ABSTRACT

A parallel plate dimensional electrical mobility separator and laminar flow water condensation provide rapid, mobility-based particle sizing at concentrations typical of the remote atmosphere. Particles are separated spatially within the electrical mobility separator, enlarged through water condensation, and imaged onto a CCD array. The mobility separation distributes particles in accordance with their size. The condensation enlarges size-separated particles by water condensation while they are still within the gap of the mobility drift tube. Once enlarged the particles are illuminated by a laser. At a pre-selected frequency, typically 10 Hz, the position of all of the individual particles illuminated by the laser are captured by CCD camera. This instantly records the particle number concentration at each position. Because the position is directly related to the particle size (or mobility), the particle size spectra is derived from the images recorded by the CCD.

13 Claims, 22 Drawing Sheets

| 18 nm | 40 nm | 100 nm | 200 nm |

AEROSOL MOBILITY IMAGING FOR RAPID SIZE DISTRIBUTION MEASUREMENTS

CROSS-REFERENCE TO RELATED APPLICATIONS

The instant application is a National Stage entry under 35 U.S.C. §371 and claims the priority benefit under 35 U.S.C. §365 of International Patent Cooperation Treat Application No. PCT/US2013/063885, filed 8 Oct. 2013, which in turn claims priority of prior U.S. Provisional Patent Application Ser. No. 61/710,858, filed 8 Oct. 2012, both under the same title and having the same inventive entity as the instant application. The complete disclosure of each prior and/or related application is hereby incorporated herein by this reference in its entirely for all purposes.

STATEMENT REGARDING FEDERALLY SPONSORED RESEARCH

This invention was made with government support under contract number DE-AC02-98CH10886 with the U.S. Department of Energy, and under Grant No. SC0006312 from the U.S. Department of Energy. The government has certain rights in the invention.

BACKGROUND

1. Technical Field

The present disclosure relates to measuring the size and number concentration of airborne particles. Specifically, this disclosure relates to rapid measurement of the particle size spectra and concentration in the ultrafine and sub-micrometer size ranges, with particle diameters from several nanometers up to about one micrometer.

2. Brief Discussion of Related Art

Most commonly, high-resolution particle sizing in the diameter range from several nanometers to many hundred nanometers is done by electrical mobility sizing. Electrical mobility methods are able to detect smaller particles than is possible by optical means, and for spherical particles the sizing is independent of unknown quantities such as particle refractive index or density.

The most common approach is differential mobility sizing, whereby a single mobility size is selected from an input polydisperse particle source by applying an appropriate voltage on a mobility drift tube. At a fixed voltage setting the particles exiting the drift tube all have the same mobility, and different sizes are selected by stepping through the voltages. At each selected size the particle concentration exiting the drift tube is measured using a condensation particle counter, which enlarges the selected particles through condensation to enable their detection by optical means. Size distributions are obtained by sequential measurements at different drift tube voltage settings, a process that can take several minutes (Liu and Pui, 1974). The scanning mobility particle spectrometer (SMPS) technique developed by Wang and Ragan (1989) has greatly improved the speed of mobility methods by rapidly scanning through the drift tube voltages, but the process still takes more than one minute to characterize an entire size distribution spectrum.

Another approach is electrometer-based mobility sizing systems, which measure multiple mobility sizes by placement of a series of electrometers along the collection electrode of the electrical mobility drift tube (Tammet et al, 1999, 2002). These instruments can measure complete size spectra at 1 Hz-10 Hz, but their size resolution is limited by the multiple charging associated with the use of a unipolar charger, and the lower concentration they can detect is limited by electrometer noise (Jeong and Evans, 2009). While they offer high time resolution, these electrometer based instruments have neither the sizing precision nor the sensitivity for atmospheric measurements, where particle concentrations aloft are often of the order of a $10^3$ cm$^{-3}$.

The differential mobility methods are capable of measurements at low particle concentrations, but are slow, requiring several minutes to complete each size distribution measurement. The electrometer-based methods are fast, but are unable to detect particles at low concentrations typical of the atmosphere, especially in background or remote locations. None of these currently available technologies provide both the time resolution and the sensitivity needed for precise, rapid measurements at typical atmospheric concentrations. This present disclosure describes a method to measure particle size spectra with the size resolution of the differential mobility methods, but with the time resolution of the electrometer methods. It enables the rapid measurement of ultrafine particle size distributions with time resolution of the order of seconds.

SUMMARY

In order to overcome these and other drawbacks and disadvantages in the present state of the art, provided according to the instant disclosure is, in combination, a parallel plate dimensional electrical mobility separator, and laminar flow water condensation to provide rapid, mobility-based particle sizing at concentrations typical of the remote atmosphere. Particles are separated spatially within the electrical mobility separator, enlarged through water condensation, and imaged onto a CCD array. The mobility separation distributes particles in accordance with their size. The condensation enlarges size-separated particles by water condensation while they are still within the gap of the mobility drift tube. Once enlarged the particles are illuminated by a laser. At a preselected frequency, typically 10 Hz, the position of all of the individual particles illuminated by the laser are captured by CCD camera. This instantly records the particle number concentration at each position. Because the position is directly related to the particle size (or mobility), the particle size spectra is derived from the images recorded by the CCD.

The present disclosure may be implemented with two types of parallel plate mobility separators: the constant voltage parallel plate electrode described by U.S. Pat. No. 7,298,486, and the wide-range, two-dimensional electrode described by U.S. patent application Ser. No. 12/877,677, presently allowed, both of which are incorporated herein by reference. The condensational particle growth may be achieved using methods described by U.S. Pat. No. 6,712,881 and U.S. patent application Ser. No. 13/218,393, both also incorporated herein by reference.

BRIEF DESCRIPTION OF THE DRAWINGS

These and other purposes, goals and advantages of the present disclosure will become apparent from the following detailed description of example embodiments, read in connection with the accompanying drawings. Some embodiments are illustrated by way of example and not limitation in the figures of the accompanying drawings, in which like reference numerals refer to like structures across the several views.

FIG. 21 shows images from monodisperse particles obtained with the wide-range electrode;

DETAILED DESCRIPTION

Overview of the AMI System

The Aerosol Mobility Imaging (AMI) System enables the imaging of particles within the gap of an electrical mobility drift tube through water condensation, laser illumination and digital imaging. As a result, the rapid measurement of particle size distributions can be achieved based on particle electrical mobility. It is effective for particles as small as 10 nm, and can cover a wide size range in a single image.

Figure 1:
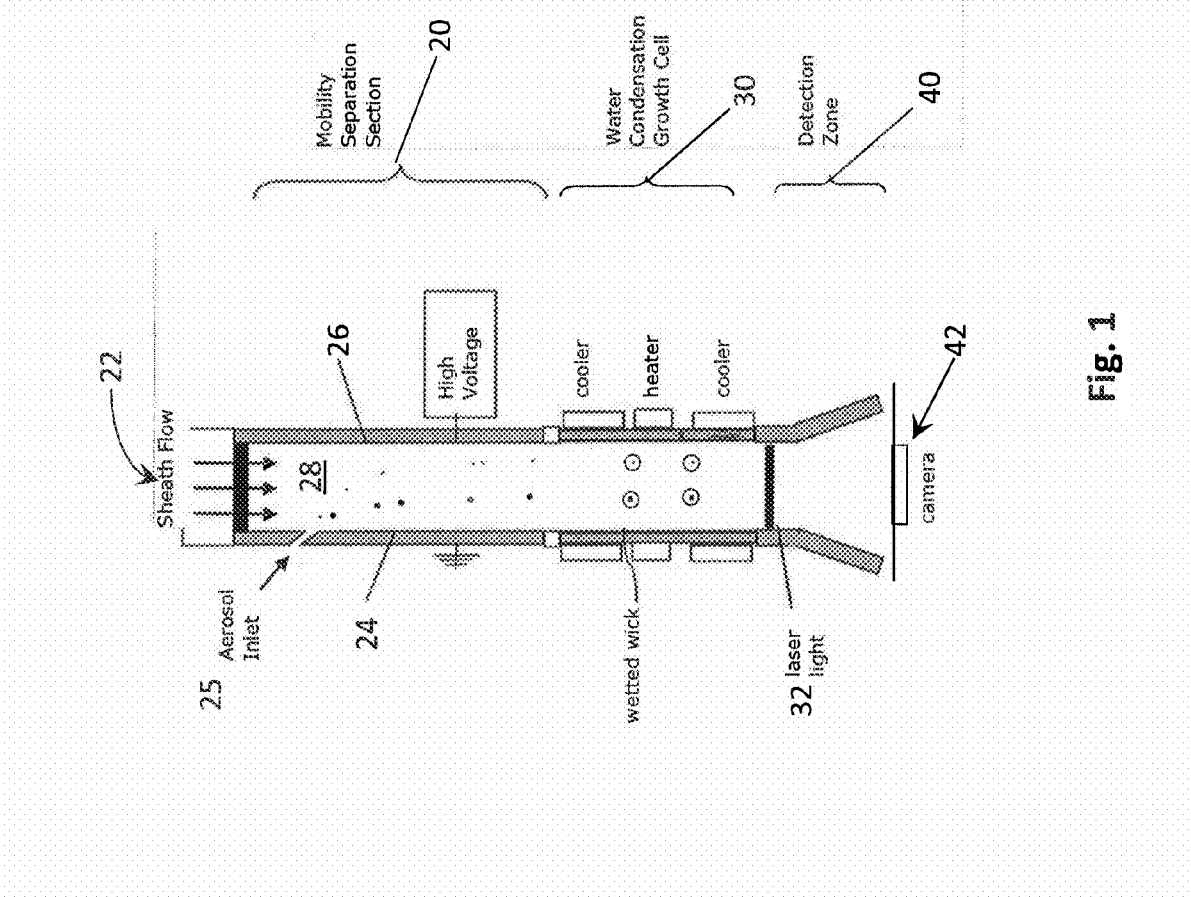
FIG. 1 is a schematic of the Aerosol Mobility Imaging (AMI) System according to a first embodiment.

FIG. 1 illustrates the Aerosol Mobility Imaging (AMI) approach of the instant disclosure. The AMI system, generally, 10, has three components; a mobility separator 20, a condensational growth section 30, and an optical detector 40. The mobility separator 20 uses a parallel plate geometry, with a laminar sheath flow 22 along the length of the electrode plates 24, 26, and an electric field applied across the gap 28 orthogonal to the direction of flow 22. Particles carrying an equilibrium charge distribution are introduced near the grounded electrode plate 24, via aerosol inlet 25. Those particles of the selected polarity are pulled across the sheath flow 22 toward the high voltage electrode 26. At the downstream end of the separation section 20, particles are distributed across the sheath flow, according to their electrical mobility.

In the AMI 10, particles exit the mobility size separator 20 into the condensational growth section 30, namely a water condensation growth cell. Here the particles are enlarged or grown to form droplets several micrometers in diameter, while continuing downstream within the gap 28 along their respective laminar flow trajectories. The growth section 30 acts as both saturator and condenser, providing the water vapor and temperature difference necessary to create the supersaturation required for activation and growth. At the end of the growth section 30, a sheet of laser light 32 illuminates the droplets, and their images are captured using an upward looking imaging device 42, e.g., a digital camera or CCD. The particle trajectory at the bottom of the separation section depends on particle diameter. The imaging device 42 captures the number of particles at various trajectories along the laser illumination path, providing number concentrations vs. size for all separated sizes simultaneously. The imaging device 42 thus records both position and number concentration of the mobility-dependent particles, from which the particle size distribution spectrum is derived. This instantly provides the number and size of individual particles that have been distributed spatially based on their mobility. In contrast to conventional approaches that scan through particle mobilities, the positions of all of the mobility-separated particles are captured at once.

The mobility separation of the AMI is roughly similar to that of the Fast Integrated Mobility Size Spectrometer (FIMS) developed by Kulkarni and Wang (2006a, 2006b, U.S. Pat. No. 7,298,486 and U.S. patent application Ser. No. 12/877, 677). However, the FIMS requires the introduction of butanol vapor in the sheath flow of the mobility separator, such that the flow into which the electric field forces the particles is nearly saturated with butanol vapor. This is then followed by a cold-walled condenser. Because butanol is a large, slowly diffusing molecule, the flow cools faster than butanol diffuses to the walls, creating a butanol supersaturation that activates the condensational growth of particles in the sub-15 nm size range. At the exit of a condenser section of the FIMS apparatus, the particles have become droplets with diameters of several micrometers. The droplets scatter enough light that they can be imaged onto a CCD array to capture their position, and hence the mobility sizes of the original particles.

In the AMI system on the other hand, the butanol condensation approach is eliminated. A new condensation cell 30 is implemented, including features in common with the laminar-flow water condensation method of U.S. patent application Ser. No. 13/218,393. In contrast to the butanol-based FIMS system, the AMI does not require the introduction of the condensing vapor in the region where the mobility separation is done. Instead the AMI uses a warm, wet-walled laminar-flow growth cell 30, which acts both as saturator and condenser. Both the sensible heat and the water vapor diffuse from the walls into the cooler flow 22.

Because water is a smaller molecule than air, the rate of diffusion of water vapor from the walls is faster than the diffusion of sensible heat. Essentially the water vapor "wins the race" into the flow 22. As a result the flow becomes supersaturated, with the maximum supersaturation at the centerline. Accordingly, the disclosed method achieves water condensational growth without disturbing the flow trajectories or particle position within the flow. In contrast, other water condensation methods such as adiabatic expansion and turbulent mixing do not maintain the laminar flow essential to the present application.

Elimination of butanol is a desirable step. Using butanol in the sheath flow introduces uncertainty in the mobility separation step, because organic particles with an affinity for the alcohol could potentially change size during the separation process occurring in the mobility separation section 20. Using water, on the other hand, this separation can be accomplished at ambient relative humidity, because the water vapor necessary for condensational growth is only introduced downstream of the separation section 20. Additionally, the water-based AMI system according to the instant disclosure opens the possibility to measure the particle size spectrum as a function of the relative humidity of the air.

There are certain practical advantages to the elimination of butanol as well. Certification of butanol-based instruments for aircraft use is becoming increasingly more difficult. Occupational health concerns have restricted the use of butanol-based counters in most routine ground based monitoring stations. Hazardous substances transport fees incurred for the supply of butanol-based instruments are significant. To appeal beyond the laboratory or research markets, particle sizing must be done without expensive or toxic working fluids.

Design of the Water Condensation Growth Cell for AMI

In one embodiment, the AMI system growth cell 30 is a Water Condensation Growth Cell, generally 100. In a first embodiment, two parallel plates are lined with a porous ceramic wick, and are positioned such that the interior width of the gap between the plates was about 11 mm. The overall length was selected at about 130 mm. It will be appreciated that these measurements are merely exemplary and not limiting on the scope of the present disclosure. To reduce the possibility of condensation on the optical components, we introduce a new "conditioner-initiator-equilibrator" architecture, for example as described in U.S. patent application Ser. No. 13/218,393. To provide smooth transition between the components held at different temperature, a new water handling method was developed, as described for example by patent application "Wick Wetting for Water Condensation Systems", filed Oct. 1, 2013. Details of the design were developed through application of numerical modeling, incorporating the effects of flow buoyancy.

Figure 2:
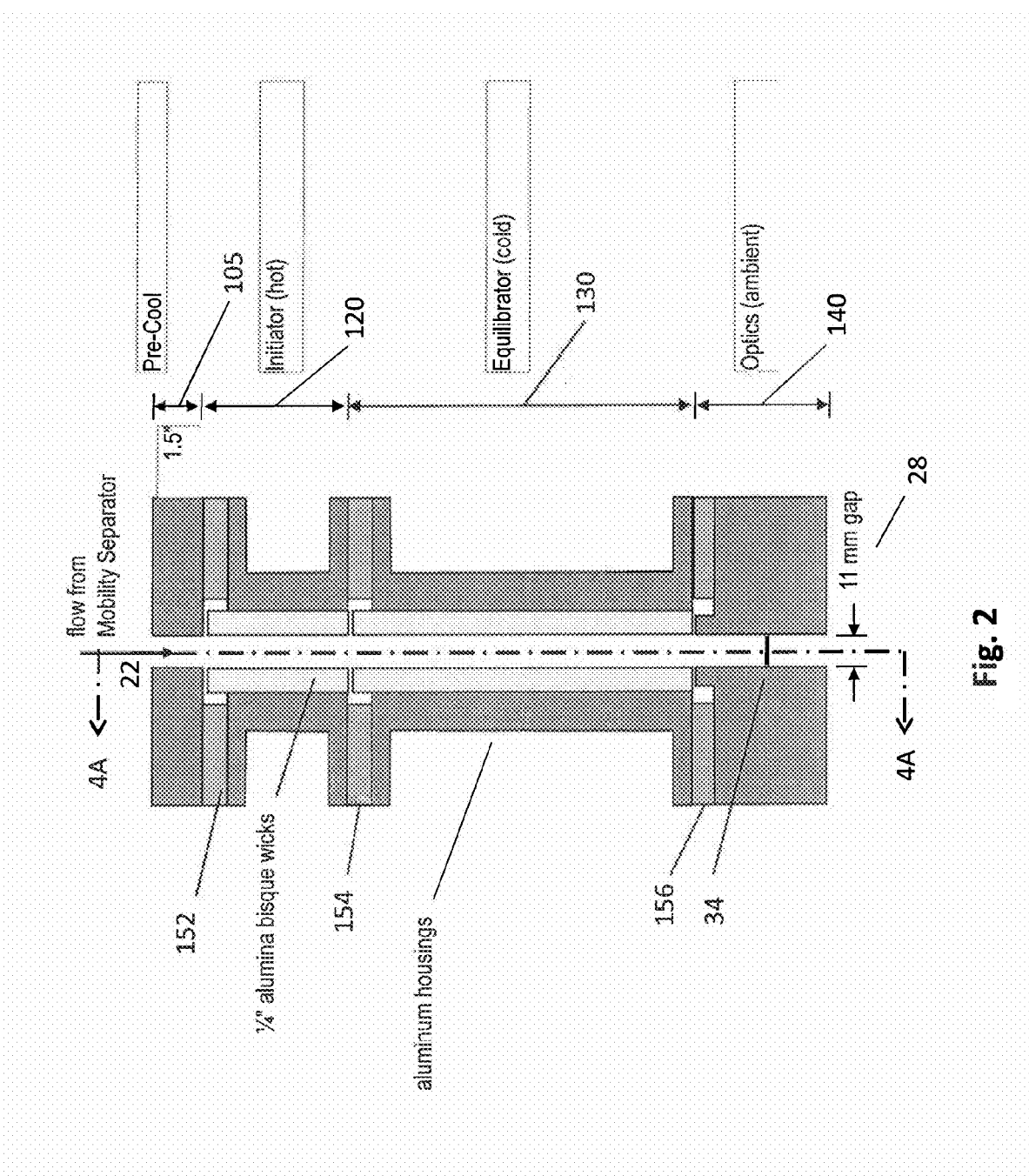
FIG. 2 shows the cross-section view of a first exemplary version of the growth cell of an AMI.

FIG. 2 illustrates the first embodiment of the water condensation growth cell 100. This embodiment uses the two-stage condenser with a warm initiator 120, followed by a cooled equilibrator 130. The warm initiator 120 section provides the water vapor that creates the supersaturation necessary for particle activation, or growth. The downstream equilibrator 130 section reduces the overall water content, while maintaining supersaturation in the flow, thereby providing the time for droplet growth while also minimizing the dew point of the flow at the optics section 140. A transition section 105 is shown, and provides temperature isolation between the condenser 100 and the preceding mobility separation section 20. We also designed the new optics section 140 to accommodate the illuminating laser light 34 immediately upstream of the imaging device 42. The names given to these various sections are: pre-cool, at ambient temperature—isolation section 105, initiator, hot—initator 120; equilibrator, cold—equilibriator 130; and optics, at ambient temperature—section 140. These housings are thermally isolated from each other by insulator pieces 152, 154, 156, which may be of a plastic or other thermal barrier material found suitable.

These components were modeled using a two-dimensional, finite-element numerical simulation developed using COMSOL Multiphysics® (COMSOL, Inc). This software allowed us to accommodate the complex geometry of the components, and to include the effects of buoyancy. We exercised the model to assess optimal size of the components and insulating pieces, to estimate heating and cooling requirements for the predicted operating temperatures needed to achieve the targeted activation and droplet growth while providing that flow exiting from the equilibriator 130 has a dew point that is below room temperature, thereby avoiding condensation on the ambient temperature optics section. The fluid flow calculations take into account the temperature-dependence of the air density and the effect of gravity (buoyancy). The water vapor concentration and temperature are calculated by a convection-diffusion model, assuming the water to be a dilute constituent, meaning the water concentration does not affect the air properties. The concentration at the wick surface is set to the saturation vapor pressure of water at the wick surface temperature. The temperature in the wick and other solids is calculated assuming the published thermal conductivity values for the various components.

Figure 3:
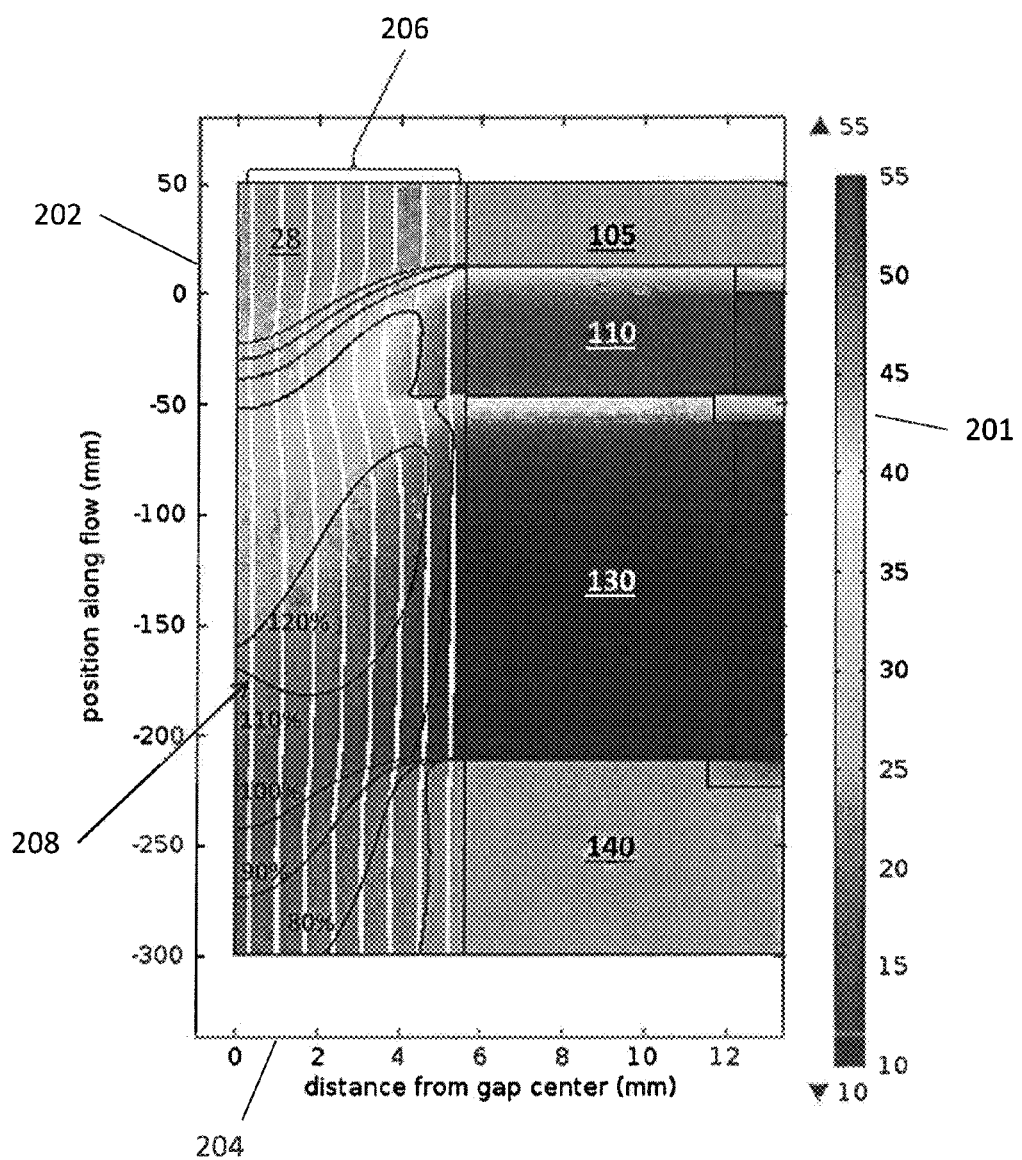
FIG. 3 shows the model flow streamlines, temperature and relative humidity for the growth cell of the first embodiment.

FIG. 3 shows a graph depicting the important results from the numerical model of the first condensation growth tube depicted in FIG. 2. In FIG. 3, the vertical axis 202 is aligned with the flow direction through the gap 28. The horizontal axis 204 indicates position relative to the center of the gap 28. Which was 11 mm wide in the exemplary embodiment. The left edge of the modeled area is a symmetry boundary at the central plane of the gap 28. The flow channel in the gap 28 was 5 inches wide, extending perpendicular to the page, and is treated as infinite. On the right side of Figure are the solid components: isolation section 105, initator 120, equilibrator 130, and optics section 140. The boundaries representing the temperature control surfaces are to the right, and are not shown. The flow entering the modeled area is laminar, at 50% RH and ambient temperature. The lines 206 extending substantially vertically through the gap 28 show the flow trajectories. The dashed lines 208 show the contours of constant supersaturation, expressed as RH. The shading indicates temperature according to the depicted legend 201. In the models, the initiator 120 was held at a temperature of 55° C., and an equilibrator 130 at a temperature of 10° C.

Additionally, the model includes a heat source on the wick-air interface corresponding to the amount of evaporation or condensation occurring. The warm initiator 120 introduces water vapor into the flow. Since the mass diffusivity of water is higher than the thermal diffusivity of air, this water vapor transport occurs more quickly than the flow warms, creating a region of water vapor supersaturation. Under these conditions the calculated peak saturation ratio is 120%, which is sufficient to activate 12 nm particles. The cool equilibrator section 130 then lowers the dew point below the optics temperature, as required to prevent condensation on the optical surfaces. Because the air temperature falls along with the dew point, the supersaturation is maintained, and the droplets will continue to grow, thereby enabling them to be imaged optically.

Figure 4A:
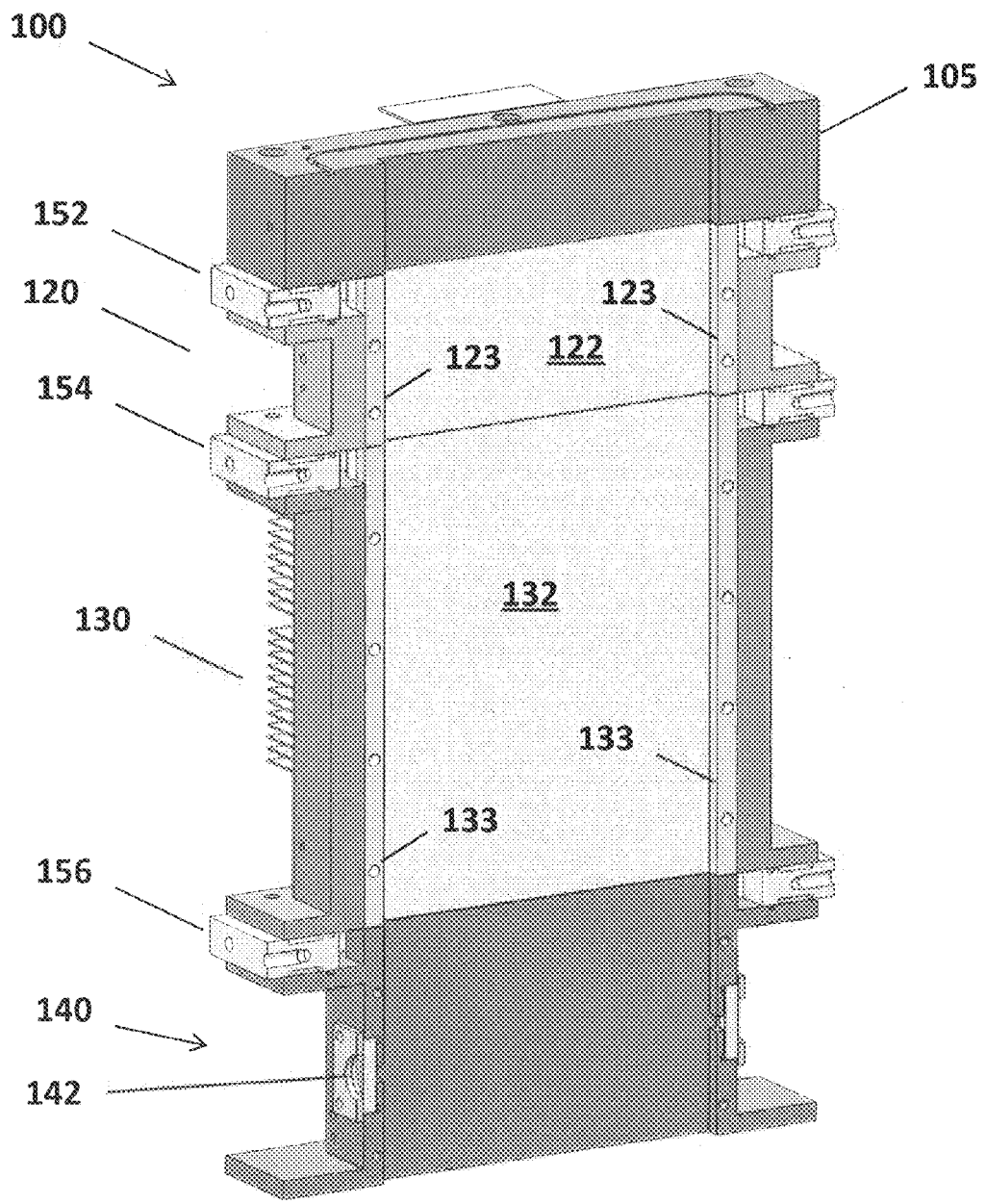
FIGS. 4A and 4B show a version of the water condensation growth cell for an AMI system.
Figure 4B:
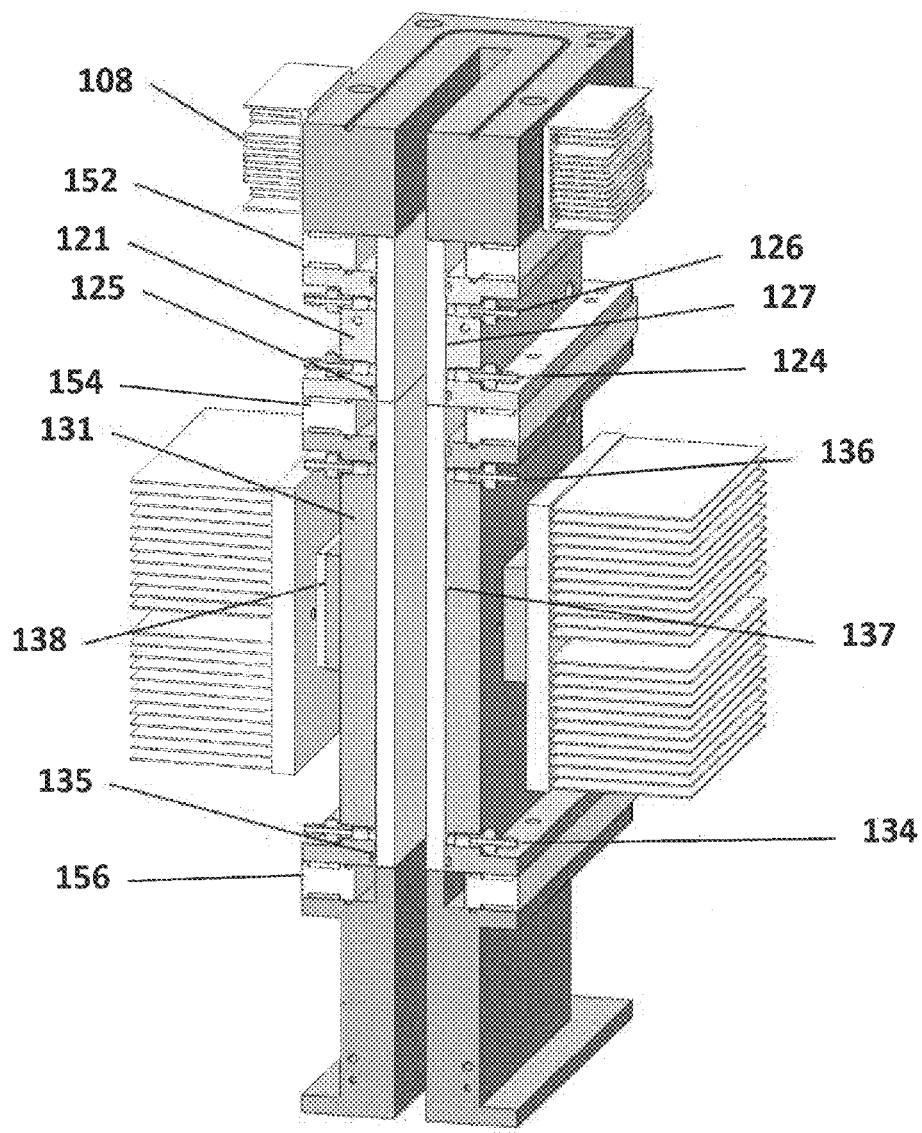

FIGS. 4A and 4B show a CAD image of the water condensation growth cell 100 described above. FIG. 4A in an internal view of the water condensation growth cell 100 taken in cross-section indicated by section line 4A-4A in FIG. 3; FIG. 4B shows a perspective view including a transverse cross-section analogous to the end view of FIG. 3. The water condensation growth cell 100 includes pre-cooler section 105 to provide active temperature isolation between the mobility separator 20 and the initiator stage 120 of the condenser. This is followed by the two stages of the condenser, initiator 120 and equilibrator 130. Each of these condenser sections 120, 130 have the walls of the gap 28 lines with separate, ¼" thick alumina wicks 122, 132. The respective wicks 122, 132 are each held by clamps 123, 133, respectively. The space between the wicks 122, 132 and the respective housings 121, 131 are sealed by sealing rings 125, 135. As disclosed in patent application "Wick Wetting for Water Condensation Systems", water fill ports 124, 134, and air purge ports 126, 136 (See, FIG. 4B) supply water to a gap 127, 137, thus created between each wick 122, 132 and their corresponding housings 121, 131. It will be appreciated that symmetrical structure is provided on either side of the gap 28.

The initiator 120 includes cartridge heaters, and the pre-cooler 105 and equilibrator 130 are equipped with a thermo-electric devices 108, 138, respectively for cooling. Thermal isolation is provided by the plastic, separators 152, 154, 156. Temperatures were controlled by programmable on-off controllers, in this embodiment Tecnologic TLZ10 (not shown).

The flatness of the channel surfaces was made a high priority. The wicks 122, 132 were formed of ¼"-thick sheets of alumina bisque, a partially-fired ceramic. The material is smooth, and it is stiff enough to be clamped in place at the edges, out of the way of the flow. It has a porosity of about 25%, and prior experience has indicated it as suitable as a wick.

According to numeric modeling, the pre-cool section 105 was determined to be an advantageous component. It is critical that the air not be heated before encountering a wet wick. In consideration of attaching the separation section 20 housing, including its polycarbonate shell, directly to the aluminum housing of the initiator, the model showed that despite the low thermal conductivity of the plastic, the airflow in the last few inches of the separator 20 would be heated enough to significantly degrade droplet growth. The actively-cooled aluminum pre-cool section 105 therefore prevents the initiator 120 from heating the separator 20. Modeling also showed that the temperature breaks between the sections could be accomplished by air gaps of about 0.01" (250 μm). The modeling shows these gaps are sufficient to limit the heat leaks to manageable levels, while not disrupting the flow. These features were incorporated in the exemplary design. The optics section 140 with laser windows 142 was newly fabricated. The existing FIMS optics section is part of the FIMS butanol condenser, and by obviating the need for butanol, the condenser portion was unnecessary.

Figure 5:
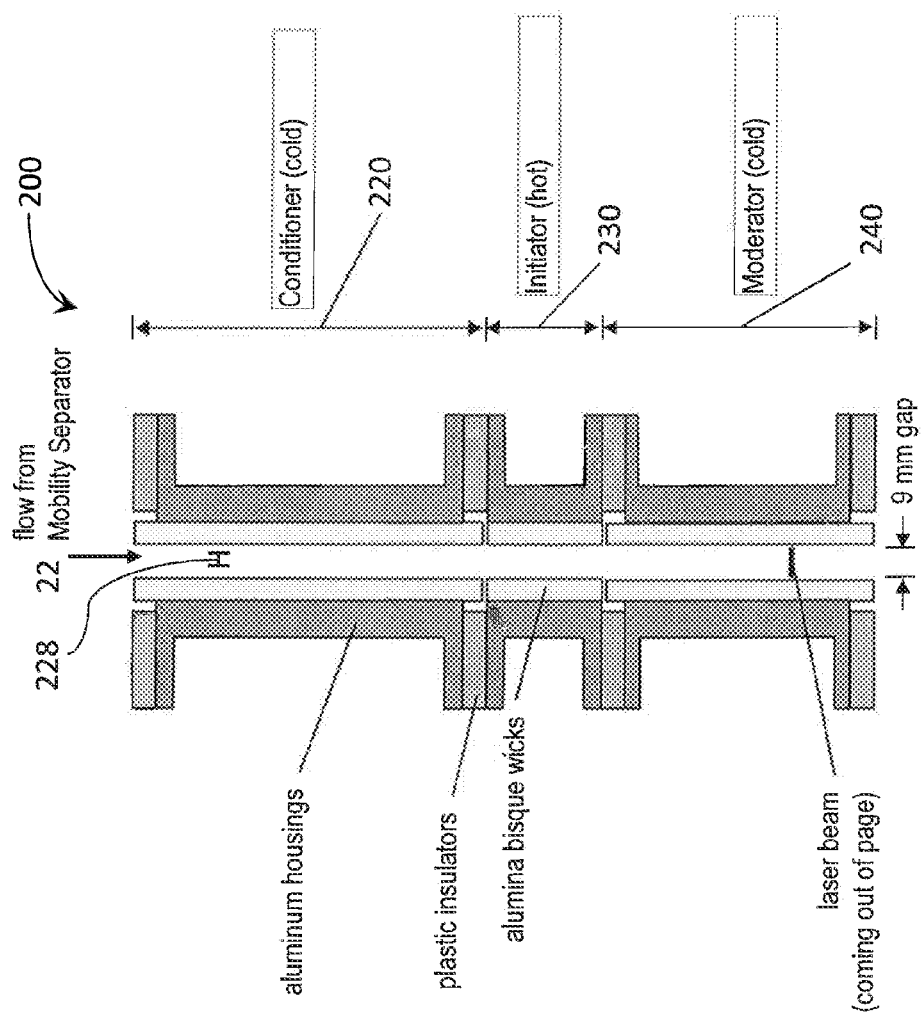
FIG. 5 shows the cross-section view of a further embodiment of a water condensation growth cell, including a conditioner stage.

FIG. 5 illustrates schematically a further embodiment of a water growth condensation cell, generally 200. This embodiment 200 differs from the prior embodiment 100 at least in that a pre-cool section 105 is replaced with a temperature and relative humidity conditioner 220, added upstream of an initiator section 230. This conditioner 220 cools the flow exiting the separator 20, for example and in certain embodiments to near 10° C.

Figure 6:
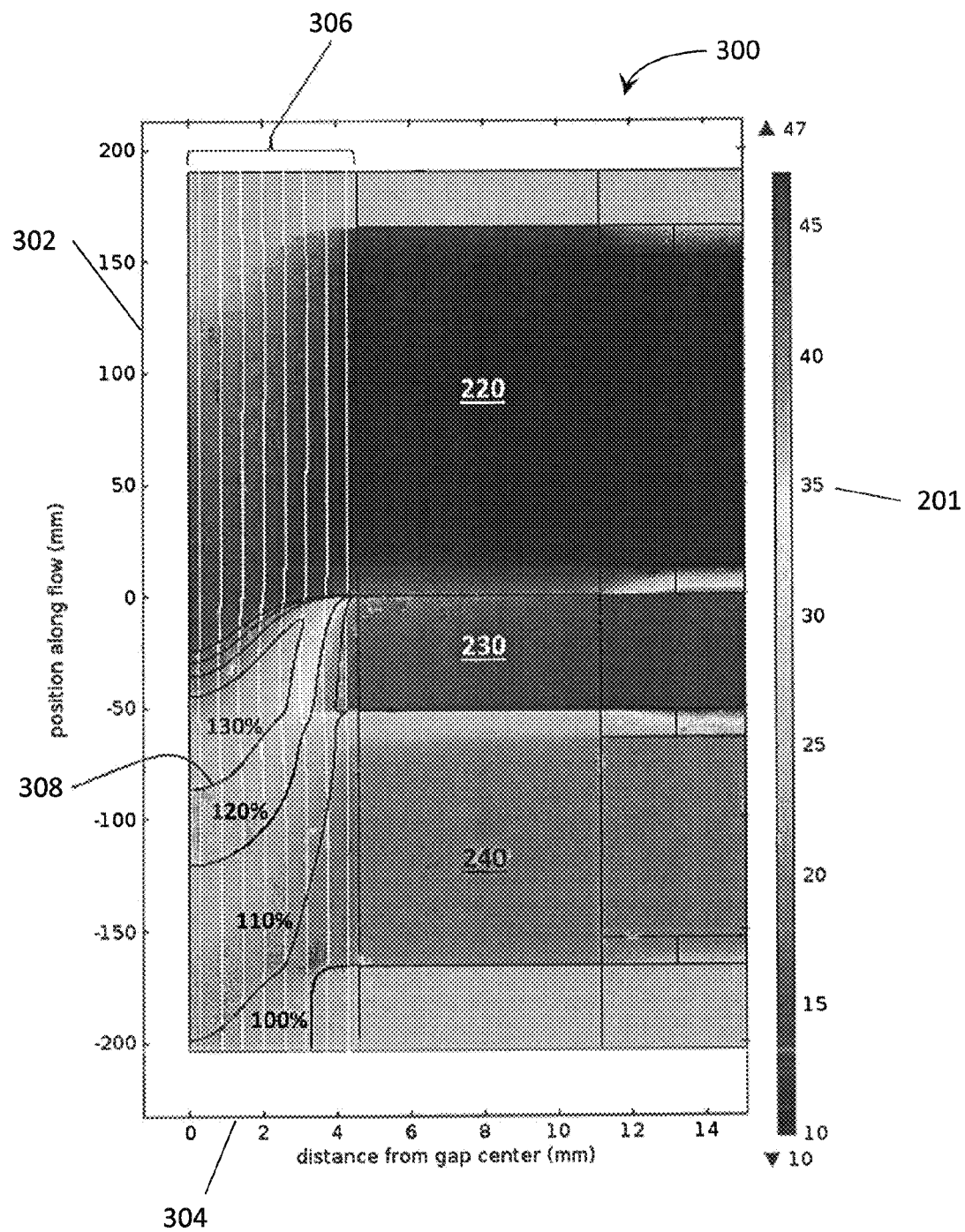
FIG. 6 shows the model results for the full growth cell system.

FIG. 6 illustrates numeric modeling results, generally 300, from COMSOL, of the embodiment depicted in FIG. 5. As illustrated in FIG. 3, the vertical axis 302 is aligned with the flow direction. The horizontal axis 304 indicates the position relative to the center of the gap 228 (see FIG. 5), with the left edge being a symmetry boundary coincident with a central plane of the gap 228. In this embodiment, the gap 228 is set to 9 mm, though other gap dimensions are within the scope of the present disclosure. Calculations were done assuming a lower relative humidity in the sheath, namely 20% RH at 24° C. The walls of the conditioner 220 are set to 10° C., those of the initiator 230 are set to 47° C., while those of the equilibrator 240 are 18° C. Saturation ratios of the fluid flow in the gap 228 are depicted by the dashed line contours 308, each labeled by their corresponding RH. Flow temperature is indicated by the shaded legend 301.

The results 300 show that even with the lower relative humidity of the sheath flow 22 entering the condensational cell 200, saturation ratios of 1.35 (135% RH) can be obtained. As in the design of the first embodiment, the dew point of the exiting flow is lower than the ambient temperature, thereby preventing condensation on the optics.

Figure 7:
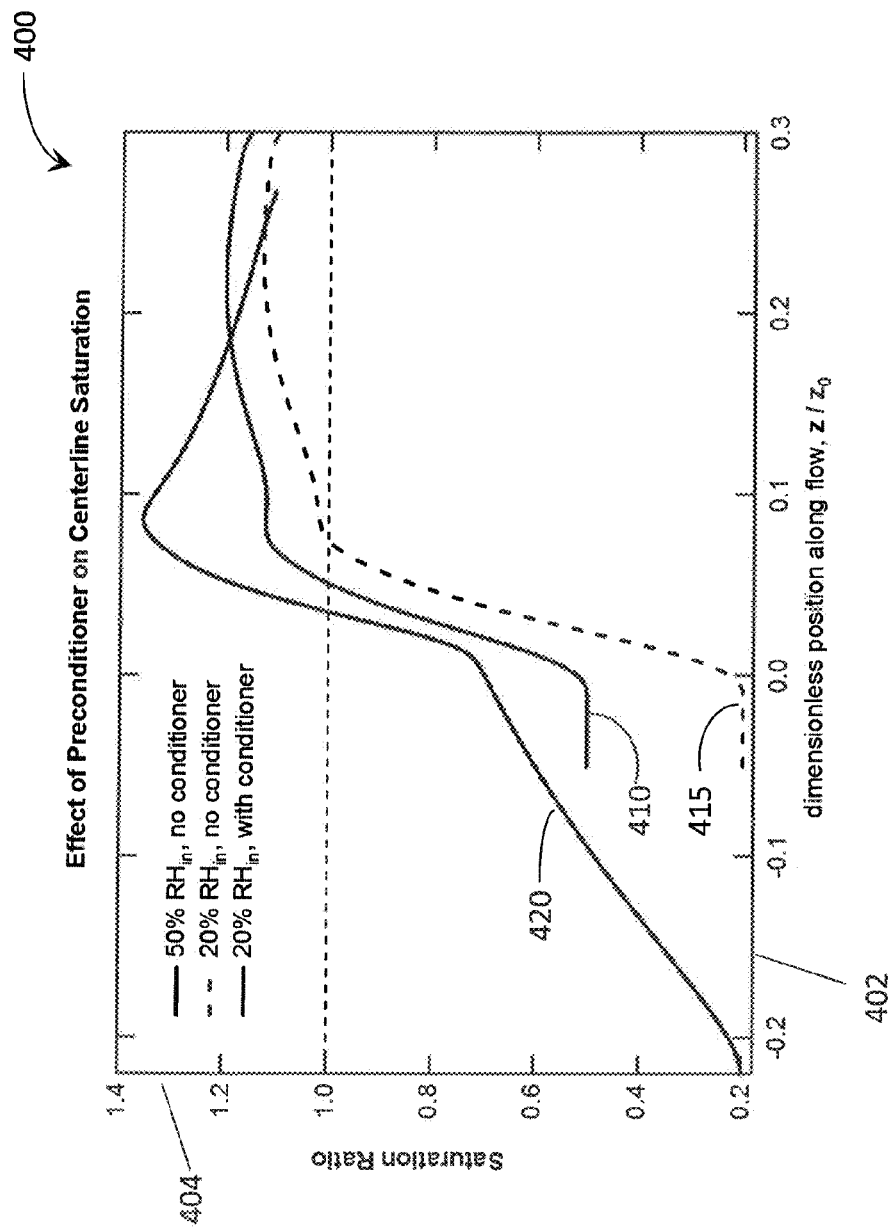
FIG. 7 compares the centerline saturation ratio, with and without the conditioner, for incoming relative humidity of 20%.

Initial studies were done with the first implementation of FIG. 3, wherein the relative humidity of the flow in the separator was near 50%. More typically in the prior art, particle sizing is done under dry conditions, and thus the relative humidity in the flow exiting the mobility separator and entering the growth cell is at or below about 25% RH. The graph depicted in FIG. 7, generally 400, illustrates the benefit provided by the conditioner of the full implementation under lower relative humidity input conditions. Plotted in FIG. 7, vertical axis 404 represent the saturation ratio along the center of the gap 28, 228. The horizontal axis 402 measures the position along the flow, z, normalized by the characteristic length, $z_0=(Q/D)(h/W)$, where Q is the volumetric flow rate, D the mass diffusivity of water, h is the gap spacing and W is the width of the parallel plates. For an input relative humidity of 50%, line 410, represents the "no-conditioner" embodiment, as illustrated in FIG. 3, modeled with an initiator temperature of 55° C., which provides a saturation ratio of 1.2. However, at 20% RH input, represented by line 415, the peak saturation ratio drops significantly. When a 10° C. conditioner 220 is added at the input, represented by the device and design depicted in FIG. 5, this embodiment achieves a saturation ratio of 1.35, even with the initiator 230 operating at a slightly cooler temperature value of 47° C. This provides better performance at a lower temperature of the Initiator, and thus with less addition of water vapor to the flow.

Figure 8:
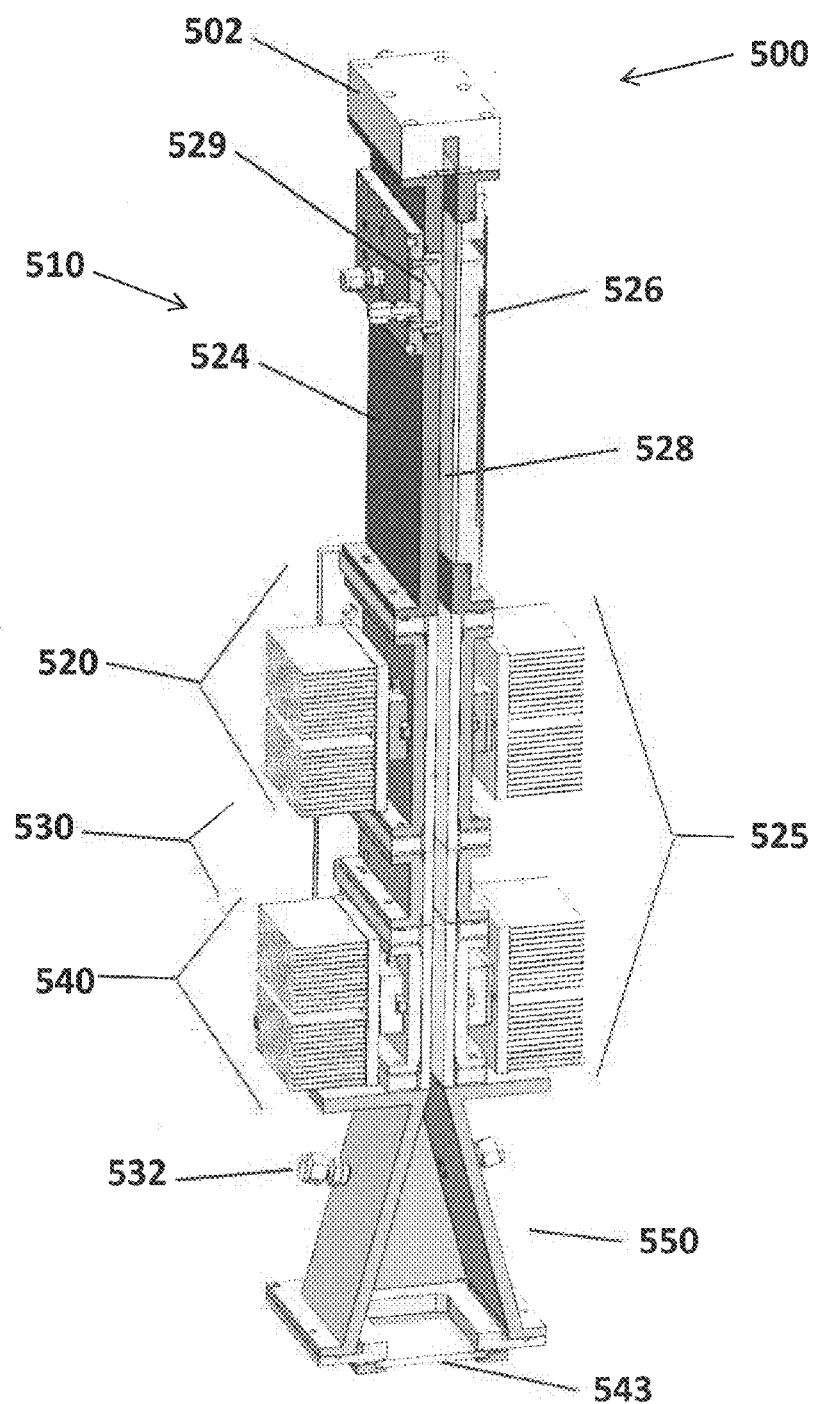
FIG. 8. Mechanical cross-sectional drawing, of the full AMI system, with sheath and aerosol flow inlets, separator section, the three-stage growth cell (Conditioner, Initiator, Equilibrator), and camera interface. The laser beam that illuminates the particles is near the bottom of the equilibrator.

FIG. 8 depicts components of the AMI system, generally 500, including the features of the growth cell 200 of the second embodiment. Describing the AMI system 500 in a flow-wise direction, particle-free air flow enters the system via sheath flow inlet 502 upstream of the separator 510 region.

Air flow containing the particles to be measured enters through the aerosol inlet 529. This embodiment 500 includes a three-stage condensational growth cell 525, comprising conditioner section 520, initiator section 530, and equilibrator section 540. Before entering the system, the aerosol to be sampled is charge neutralized using a bipolar ion source, which puts a known charge distribution on the particles. This aerosol sample flow is evenly distributed via an inlet slit 525 across the grounded plate 524 of the separator 510, where the aerosol joins the Sheath flow which fills most of the gap 528. In one example, the sheath flow rate is within a range of about 10-20 L/min, while the aerosol flow is within a range of about 2%-5% of the sheath flow value.

After introduction, the aerosol particles are carried in the direction of the flow (downwards, in FIG. 8). The aerosol particles that are charged move sideways in response to the applied electric field from electrode 526. At the downstream end of the separator 520, the particles are distributed across the gap 528 in accordance with their electrical mobility. These mobility-separated particles enter the conditioner 520, which cools and humidifies the flow in preparation for condensational growth. The flow then enters the initiator region 530, where it encounters a region of water vapor supersaturation that initiates the particle growth in the eventual form of droplets. This initiator section is relatively short compared to the lengths of the conditioner 520 and the equilibrator 540. Following the initiator 530 is the equilibrator section 540, which provides the time (and hence distance) needed for particle growth, while also reducing the water content of the flow. In this region the particles continue to grow into the form of droplets. When the particles are droplets, they are then illuminated with a laser (not shown) and photographed using an imaging device 542, e.g., a digital camera and/or CCD via imaging window 543. The flow then exits through ports in the imaging interface section 550. The system 500 may include microprocessor and computer controls for maintaining flows, controlling the sheath humidity, setting the electrode voltages, capturing camera frame images, and other desirable parameters, which are also not shown.

Experimental Evaluation

Figure 9:
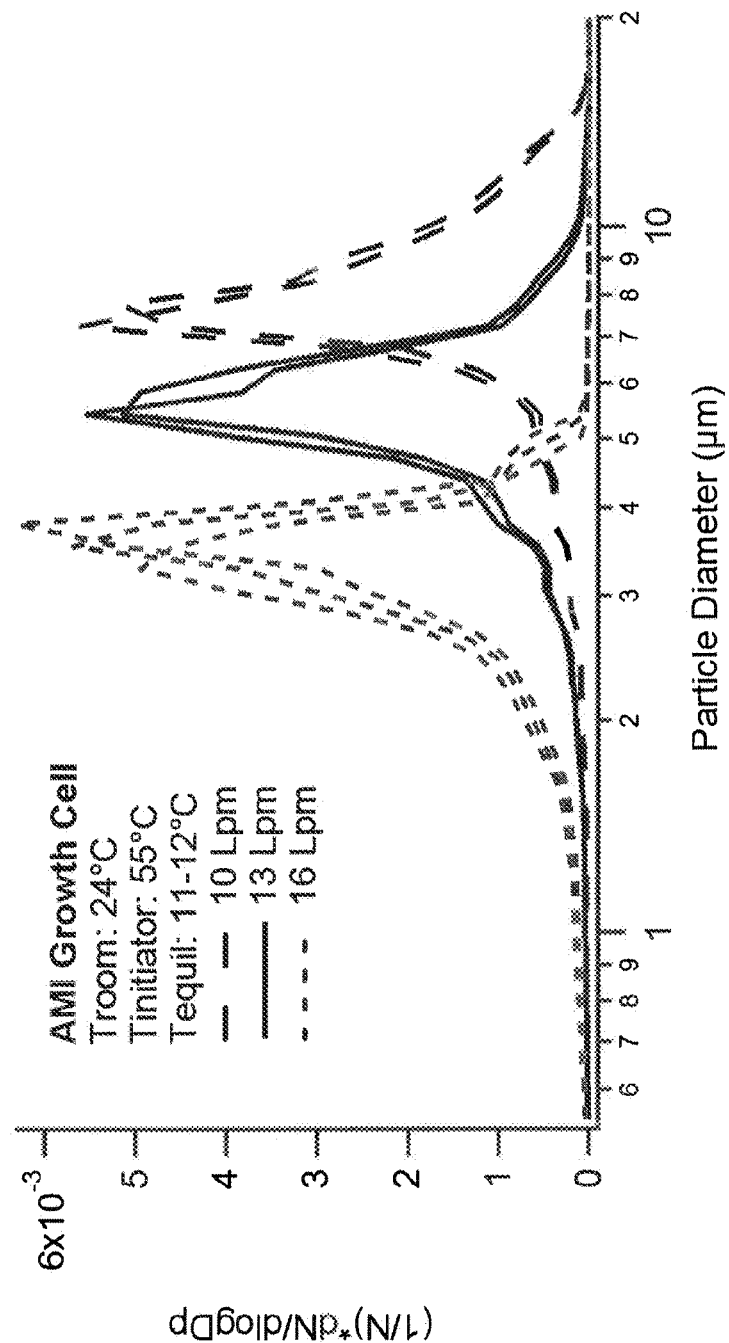
FIG. 9 shows the droplet diameters produced by the growth cell at an initiator temperature of 55° C. at flow rates of 10, 13 and 16 L/min. Inlet temperature is 24° C.; equilibrator temperature is 11-12° C., as measured by an aerodynamic particle sizer.

Performance of the first embodiment parallel plate condensation growth cell 200 designed for AMI system 10 was evaluated independently using an aerodynamic particle sizer (APS, TSI model 3321) to measure the size of the droplets formed when sampling partially filtered room air. The APS measures the size and concentration of particles in the 0.8-10 μm size range. Parallel measurements were made with a condensation particle counter (CPC, TSI Model 3785), which detects particles as small as 0.005 μm. For these tests the input particle concentrations were near ~1000/cm$^3$, which is typical of what is to be expected in the AMI system 10. The test results are presented in the graph of FIG. 9. For this data set, the initiator temperature was set to 55° C., and the flow rate was varied from 10 L/min to 16 L/min. As shown by the data, the droplet size increases for lower flow rates, corresponding to longer residence time for growth. The droplet concentration measured by the APS was comparable to the upstream dry particle concentration measured by a condensation particle counter, with a mean ratio of APS to CPC concentration of 0.98±0.02, indicating efficient activation and growth of particles sampled.

To evaluate the AMI system 10, a condensation growth cell 200 was mated to the FIMS developed at Brookhaven National Laboratory. Tests were conducted with monodisperse sodium chloride and polydisperse ambient aerosols. These tests were designed to evaluate the laminar character of the flow; shifts in measured particle position with input particle size; detection efficiencies as a function of particle size; comparison to a traditional scanning mobility particle spectrometer (SNIPS); and time response.

Figure 10C:
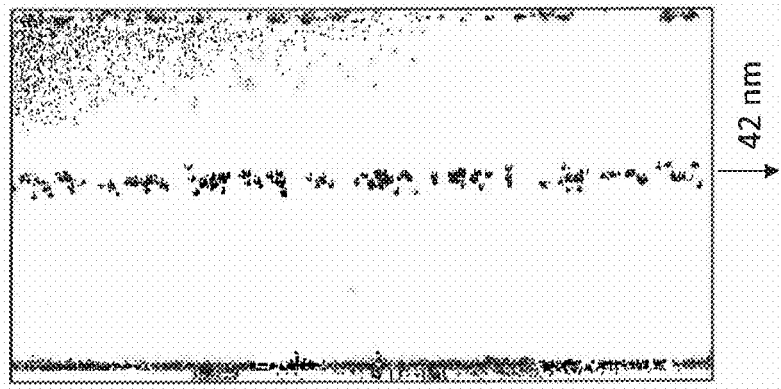
FIGS. 10A, 10B and 10C are images obtained of 100 nm, 65 nm and 42 nm DMA classified NaCl particles, respectively, in a prototype embodiment of the AMI, with horizontal rule indicating distance across the gap.
Figure 10B:
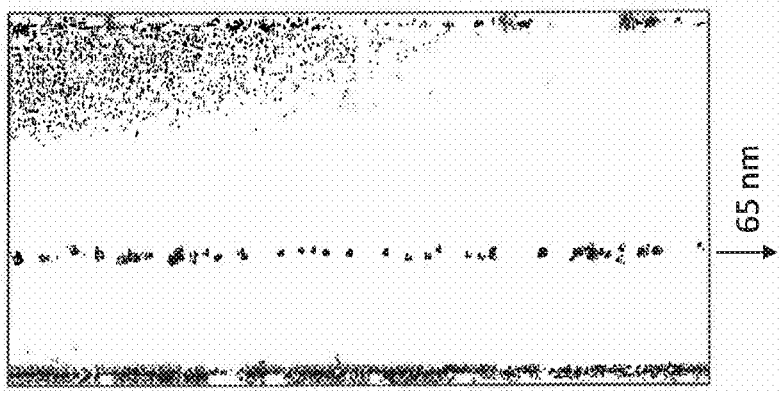
Figure 10A:
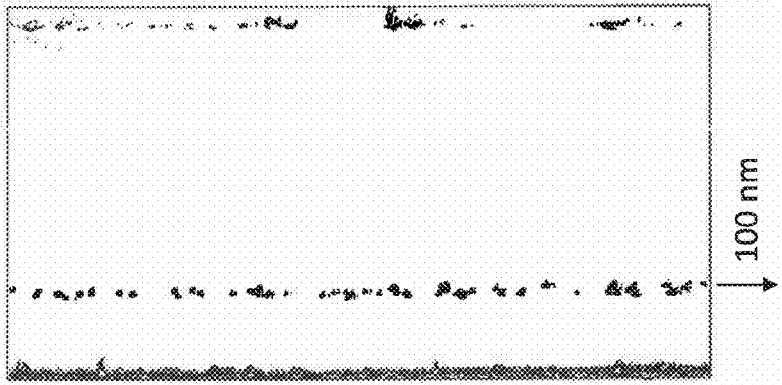

The initial tests were conducted with the mobility separator 20 configured with a simple electrode design that provides a constant electric field across the gap. The test aerosol was monodisperse sodium chloride. FIGS. 10A, 10B, and 10C show images obtained by the imaging device for three different input particle sizes, namely 100 nm, 65 nm, and 42 nm, respectively. The clear, sharply aligned particles, whose position shifts with size, indicate that the flow remains laminar. Note that the AMI provides well-defined lines, and the shift in particle position to the right for smaller particles. This is as predicted by theoretical analysis of the separator region (Kulkarni, P., & Wang, J., 2006a).

Were one to view the testing results as a movie, it would be possible to see the images of the particles shift as the upstream differential mobility analyzer (DMA) selection voltage is adjusted to shift this size of the particles entering the aerosol inlet from one size to the next. With the AMI, the change in the input particle size produces a shift in particle position that can be viewed in real time. It is reminiscent of watching an amateur chorus line, all perfectly aligned until given the signal to move, then advancing in a somewhat ragged manner until realigning themselves neatly and precisely in their new positions.

Figure 11:
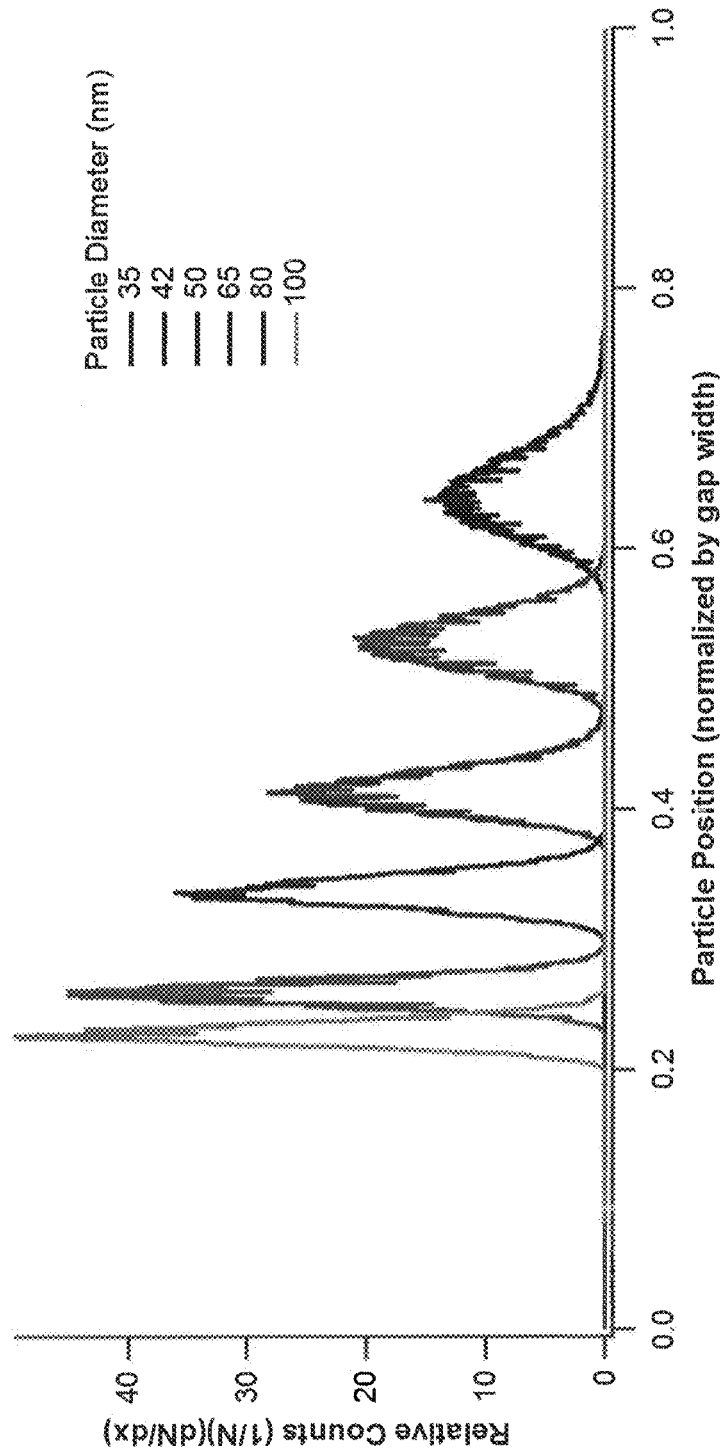
FIG. 11 is a frequency distribution of particle concentrations vs. position in the mobility separator for 6 sizes of monodisperse sodium chloride aerosols.

FIG. 11 is a frequency distribution plot of the normalized particle concentration as a function of position for six different mobility sizes tested. These data were collected at a single separation voltage. The largest particles, at 100 nm, are on the left, near the position where the aerosol is introduced. The smaller particles travel across the sheath flow and are found on the right. The peaks are all clearly separated. The width of each peak is a measure of the combined resolution of the DMA used upstream and that of the AMI. DMA-classified particles have a finite range of mobility, and the spread in their position increases with the distance travel in the direction of electric field (i.e., particle position).

Figure 12:
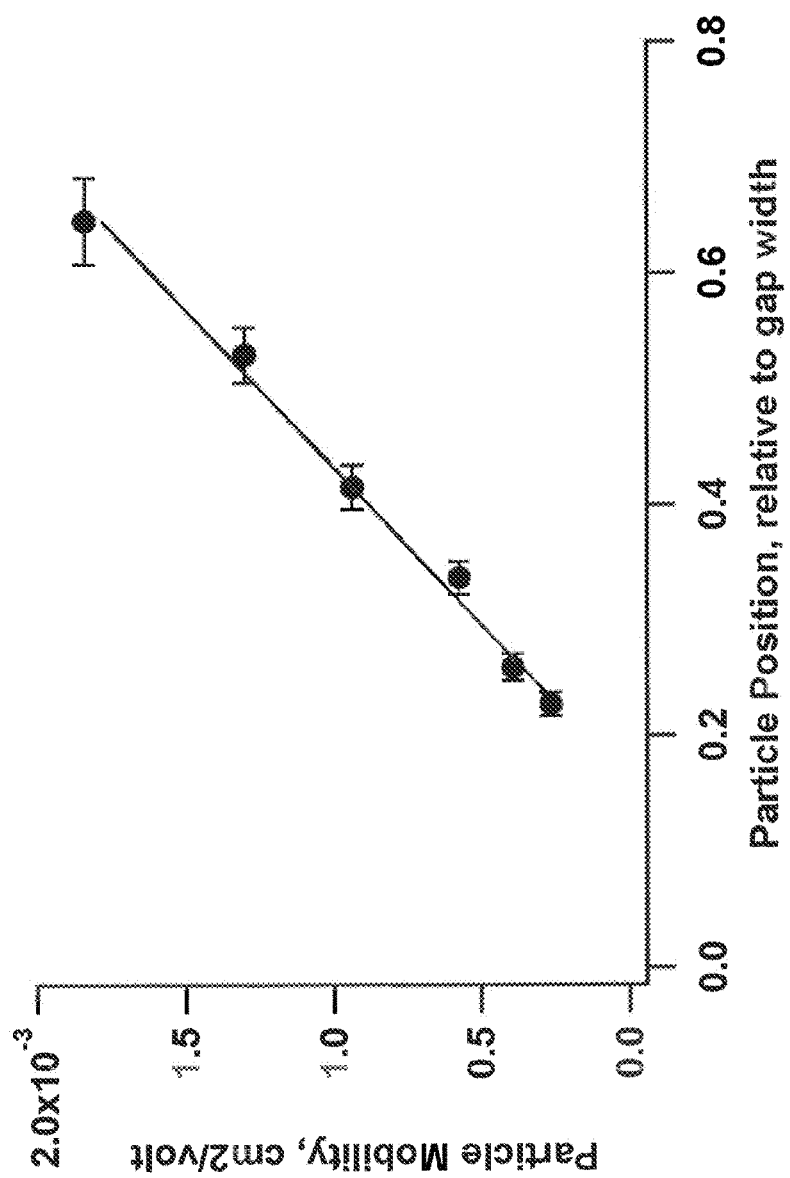
FIG. 12 shows the particle mobility vs. mean position for the data of FIG. 12, with error bars indicating the peak width at half-height.

FIG. 12 plots the particle position as a function of the particle electrical mobility for these data. With this parallel plate geometry one expects a linear dependence of the position on mobility. This linear dependence is observed for the AMI system, although there is an offset that is not yet understood. The error bars show the spread in position, derived from the width of respective peaks at half-height. This width reflects the combined transfer function from the long DMA used to generate the aerosol, and from the AMI. We note that the observed width from the AMI, which is approximately 10% of the mobility, is what is expected of the upstream DMA, as it was operated with a 10:1 ratio of sheath to aerosol flow. This means that the precision of the AMI is at least comparable to that of the DMA, and possibly much better. More detailed analysis would presumably resolve the AMI transfer function (see Kulkarni and Wang, 2006a and 2006b).

Figure 13:
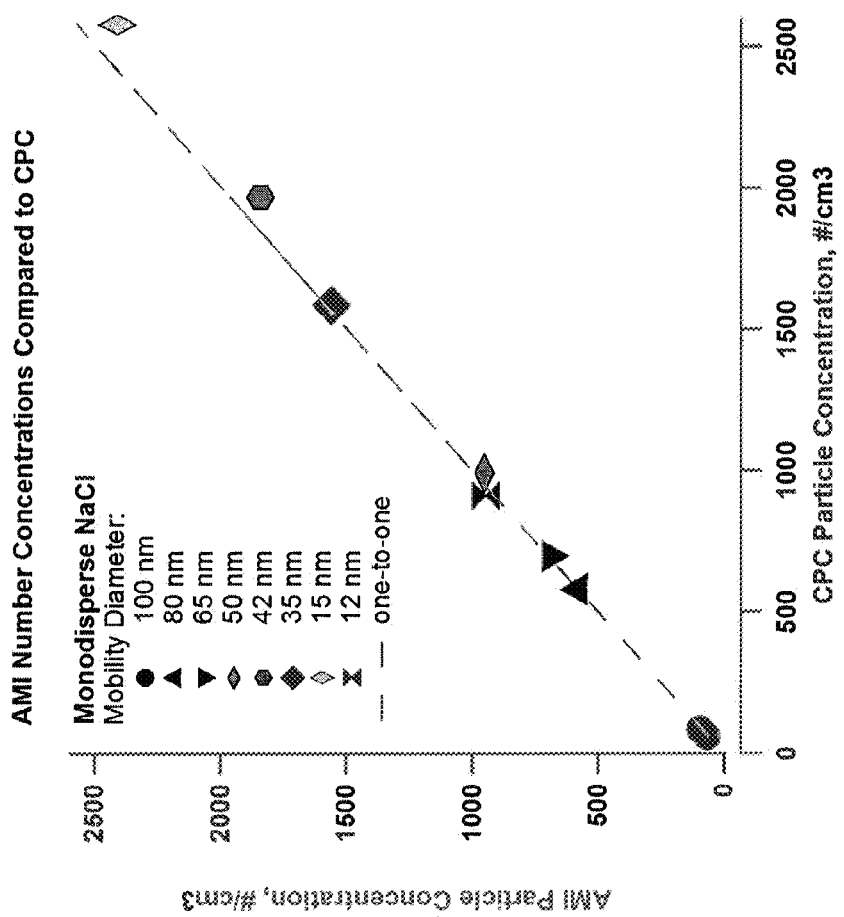
FIG. 13 shows the particle number concentrations measured by AMI compared to parallel measurements with a TSI-3025 ultrafine butanol-based condensation particle counter.

FIG. 13 shows the AMI particle detection efficiency as a function of particle size. These data show the concentration of each of the monodisperse aerosols tested as measured by the AMI, with comparison to the concentration as measured by a standard, butanol condensation particle counter (TSI 3025A). By sampling mobility size-selected aerosol, which is already charged as it exits the differential mobility analyzer, and by using the AMI without its charge neutralizer, we can directly measure the detection efficiency by comparison to a condensation particle counter, without considering the charging efficiency. Data at particle sizes from 35-100 nm were obtained at a fixed operating voltage (700V), while those for the smaller sizes were classified using lower voltages of 40 to 100V. At the smaller sizes the data are corrected for transport losses in the mobility separator.

The mean AMI detection efficiency was 100±6% across all sizes measured, from 12 nm to 100 nm. Also note that these measurements span a range of particle concentrations, from 100/cm$^3$ to 2500/cm$^3$. As these are monodisperse aerosols, all particles of the same size appear at the same gap position. This is an extreme test of particle counting coincidence, yet the AMI is able to measure aerosols of high concentrations at a single size.

In a second test battery, size distributions measured by a prototype-AMI 10 were compared to a traditional SMPS operated with the TSI long DMA column and a butanol ultrafine condensation particle counter (Model 3025). The input is diluted, ambient laboratory aerosols, obtained by mixing with dry, house air. Periodically the aerosol concentration was modulated to zero by increasing the fraction of dilution air.

Figure 14:
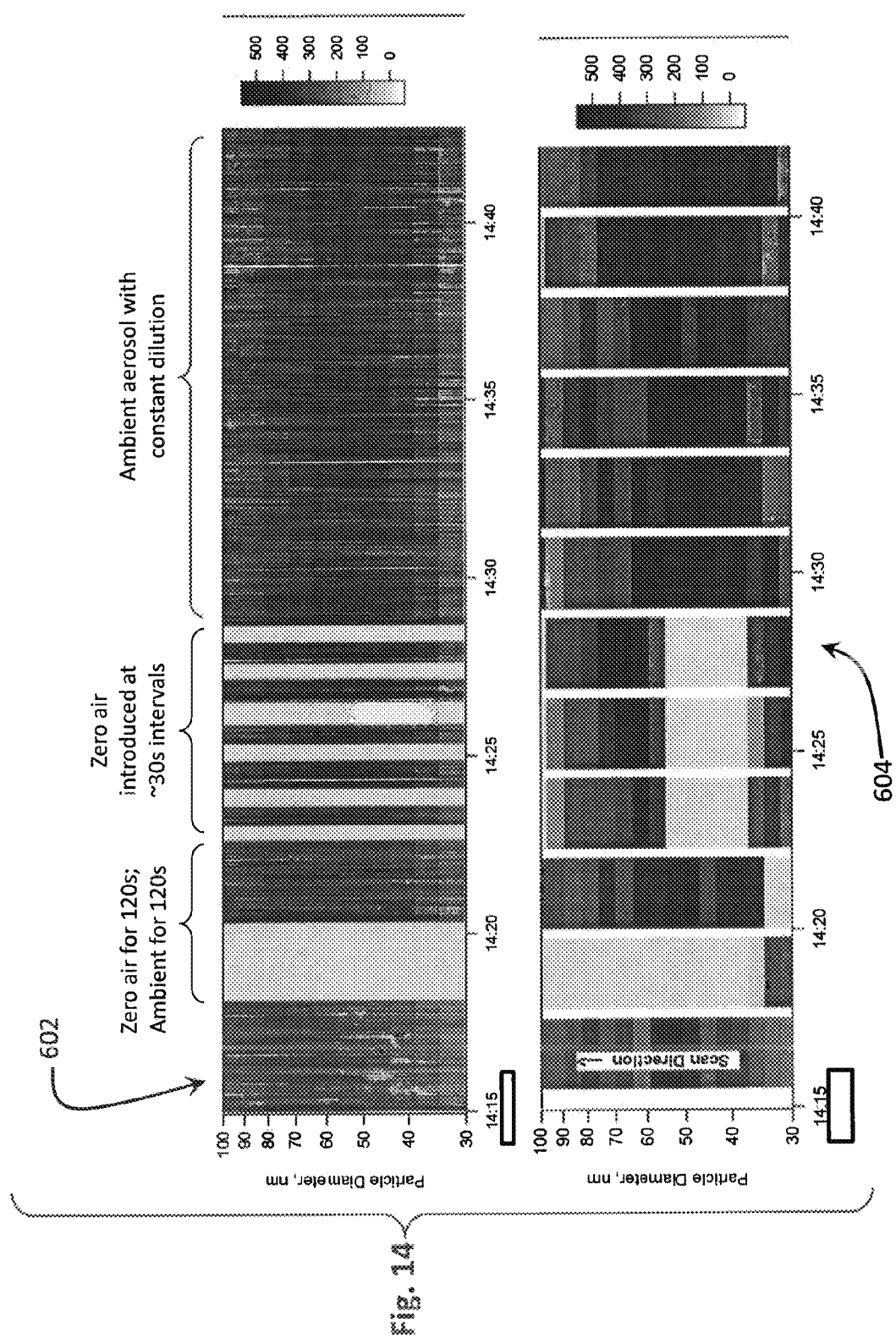
FIG. 14 shows the comparison of the 1-Hz size distributions from the AMI (top) with concurrent 2-min SMPS measurements (bottom)

FIG. 14 shows an example time series of these comparisons of size distribution data. The light bands correspond to periods of particle-free zero air. The latter part of the graph shows data at a fixed dilution level. The AMI data, i.e., the top series 602, reports a size distribution each second, while the SMPS system, i.e., bottom series 604, requires 120 seconds to scan through its 20 to 120 nm size range. As a result, when the concentrations fluctuate rapidly, the SMPS misinterprets these fluctuations as features in the size distribution. The gaps in the SMPS data correspond to the 15-s dead-time needed to return the separation voltage to its starting point, i.e., the down scan.

Figure 15:
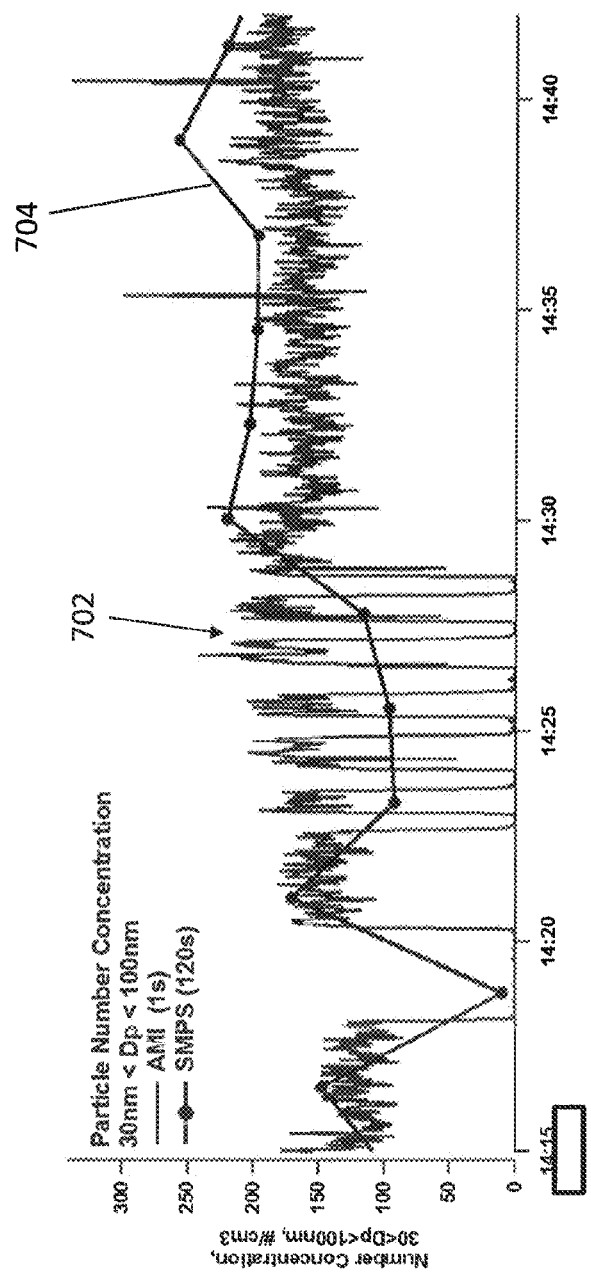
FIG. 15 shows the comparison of integrated number concentrations in the 30-100 nm size range as measured by the AMI and the SMPS, corresponding to the size distributions of FIG. 14.

For the data set of FIG. 14, both the AMI and the SMPS provide total number concentrations, as well as size distributions, for particles with mobility diameters from 30 nm to 100 nm. Comparisons of these particle number concentrations for these data are shown in FIG. 15. For the SMPS, data series 704, shown are the concentrations at each 120 s measurement period. For the AMI, data series 702, the data are at 1 Hz resolution. The introduction of zero air, and the resulting concentration fluctuation, is clearly seen in the AMI data 702.

Figure 16:
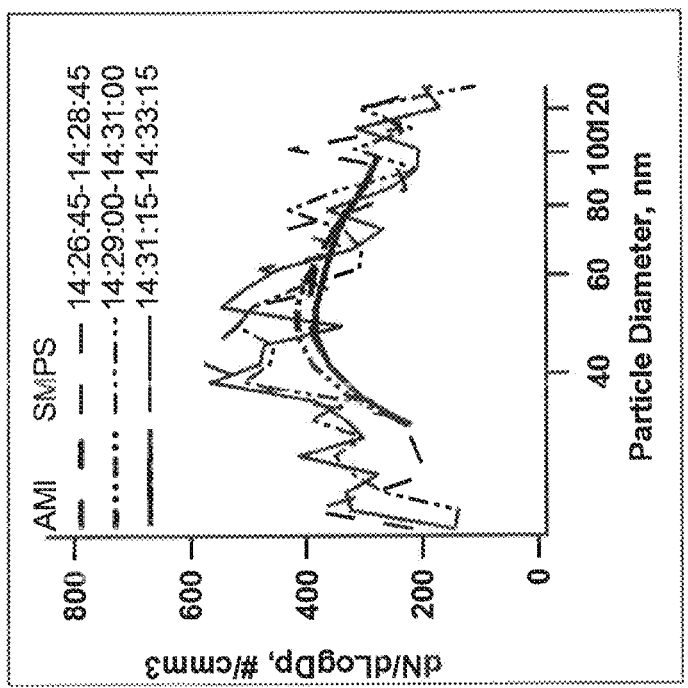
FIG. 16 shows the comparison of averages of 120, 1-sec AMI size distributions with the parallel SMPS scans for sampling ambient laboratory air.

FIG. 16 compares 2-min averages of the AMI size distribution to the parallel SMPS measurement. For stable aerosol input, both the SMPS and the AMI report number median diameters of 55-58 nm. However, at these low concentrations, the SMPS data is much noisier.

Figure 17:
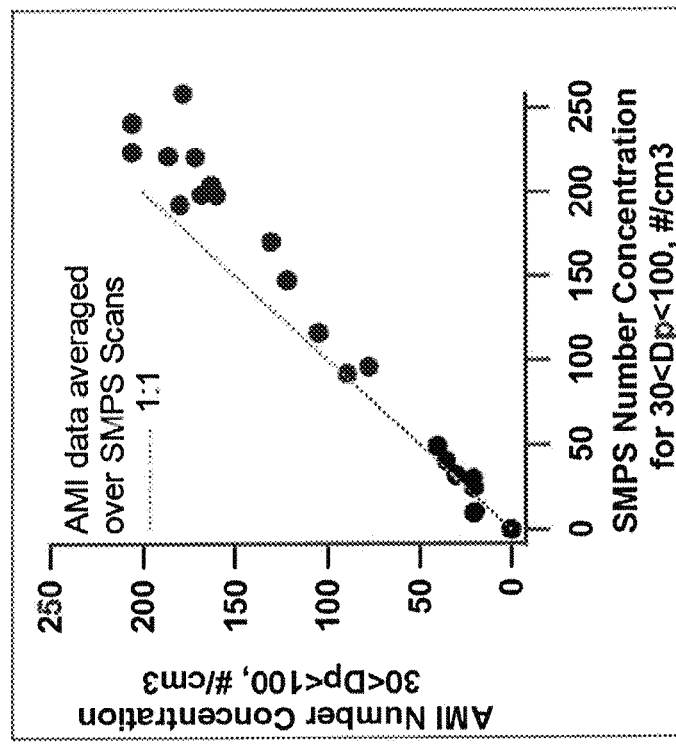
FIG. 17 shows the total number of particles with diameters between 30 nm and 100 nm, as measured by AMI and SMPS.

FIG. 17 compares the number concentrations integrated over the size range of 30 to 100 nm for the two instruments, where again the AMI data have been averaged over the 120 s window of the SMPS scans. The data are tightly correlated, with 15% lower concentrations, on average, from the AMI. We have not confirmed the source of this discrepancy, but hypothesize that the discrepancy can be attributable to the difference in the sheath flow relative humidity values for the two instruments. In these experiments, the AMI sheath flow was 50% RH, whereas the SMPS operated at the input relative humidity, which was likely below 10% due to the dilution air).

Figure 18:
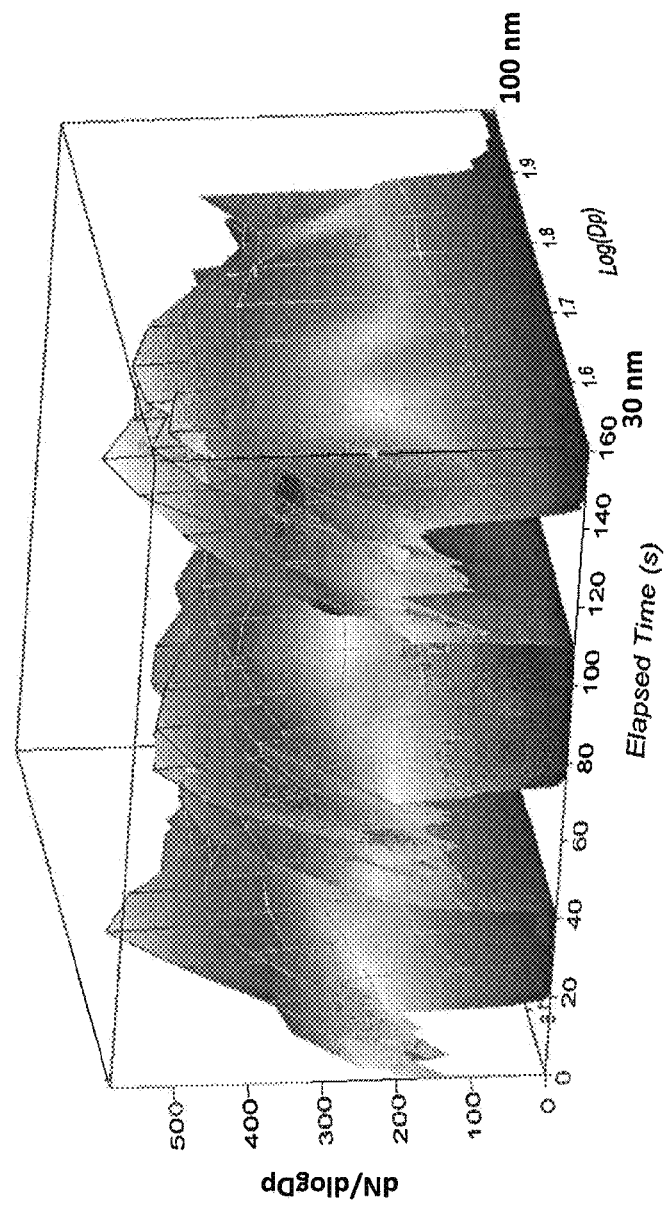
FIG. 18 displays 2.6 minutes of AMI size distribution data at 1 Hz, with 3 instances of switching to zero air. Vertical axis is dN/d log Dp.

To test the time response of the AMI, we sporadically flooded the inlet line with zero air, much as done by Olfert and Wang (2009). FIG. 18 is a surface plot of the 1 Hz AMI data over the 160-sec time period starting at 14:22, when ~30 sec of zero air were introduced at three different times. The introduction of zero air is quite pronounced. The graph also illustrates the density of the AMI data set—during this same time period the SMPS would have completed just one complete size distribution, plus one-quarter another.

Figure 19:
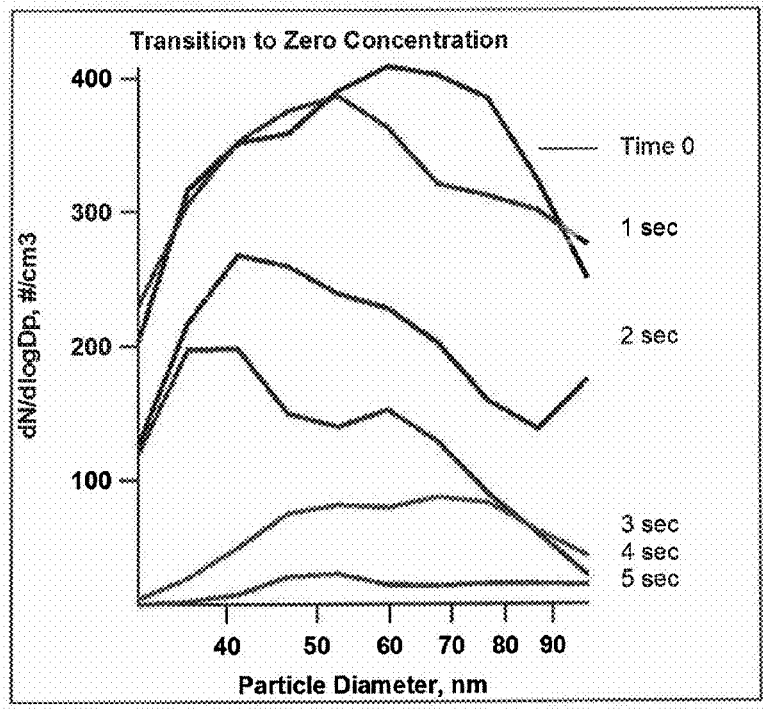
FIG. 19 shows a succession of 1-sec AMI size distributions when the input particle concentration is modulated to zero.

FIG. 19 shows 6 successive 1-sec size distributions from one of these instances. Note that the size distributions are stable, with similar shapes among successive distributions. Clearly the counting statistics are sufficient within the 1-sec window to measure the size distribution even though the concentration is just 200/cm$^3$. Second, the concentrations drop rapidly, with near-zero concentrations achieved within 5 seconds.

Figure 20:
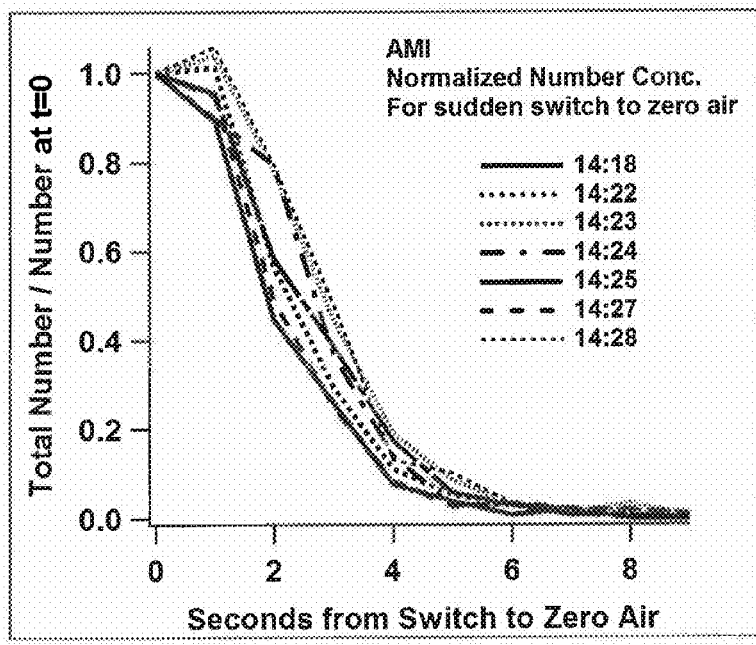
FIG. 20 shows AMI number concentrations normalized by the initial value when switching to zero air, acquired at times listed in inset.
Figure 21A:
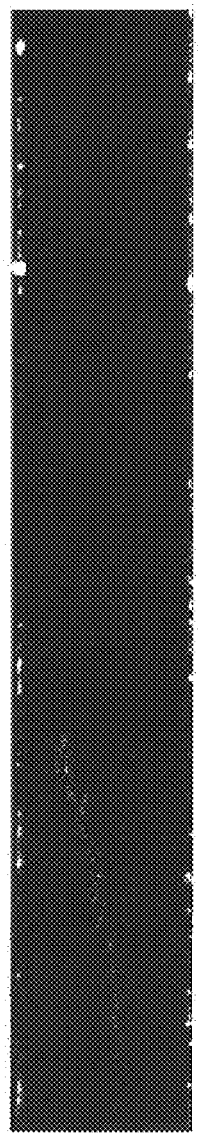
FIGS. 21A, 21B, 21C and 21D shows composite traces for particles of 13 nm, 40 nm, 100 nm and 400 nm, respectively.
Figure 21B:
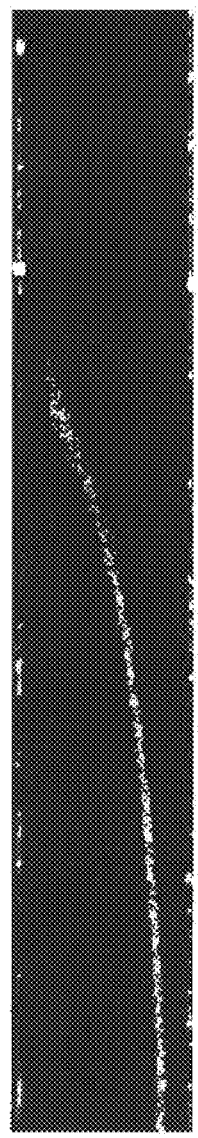
Figure 21C:
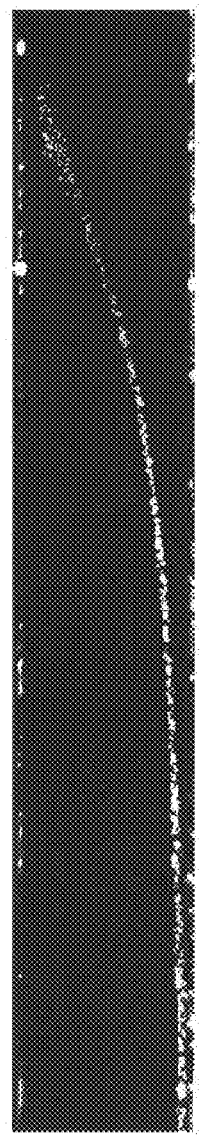
Figure 21D:
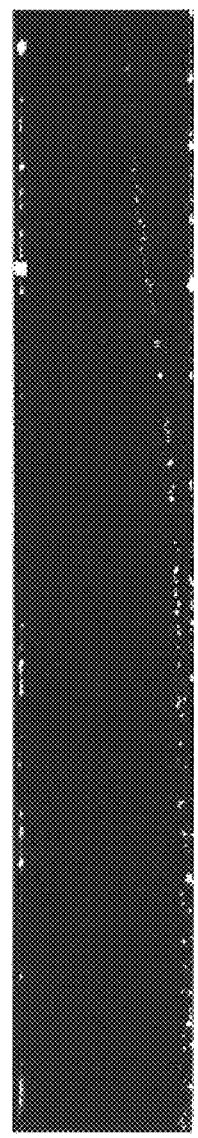

FIG. 20 shows the drop in total number concentration measured by AMI for all 7 instances of zero air introduction, where the AMI concentrations are normalized by the initial value when switching to zero air. The time constant for the decay is 2.5 s, obtained by an exponential fit to the data. This is as fast, or faster, than many CPCs, yet provides a complete size distribution from 30-100 nm.

Tests were also conducted with the two-dimensional electrode described by Wang (2009). By applying an electric field that varies from one end of the gap to the other, along the width of the parallel plate, Wang shows that a much wider range of particle sizes can be resolved. This concept was tested using an electrode formed by laying traces on a printed circuit board, to which the varying electrical potential are applied. The two-dimensional electrode tested here consists of 60 traces, with exponentially stepped electrical potentials that provide a variable electric field across the width of the separator. This provides separation over a factor of 1000 in mobility, or from 10 to 600 nm in particle diameter. For comparison, the 1D system electrode provided a separation a factor 10 in mobility, or 30 to 100 nm at a single voltage setting.

With this two dimensional electrode, theoretical analysis predicts that uniformly sized particles will align along arcs. As before, the efficacy of the approach was tested using monodisperse sodium chloride aerosols. Example results are shown in FIGS. 21A, 21B, 21C, and 21D, which display camera images of the enlarged particles for four different input sizes. For these tests the AMI was operated with a 10 L/min sheath flow at 20% RH and 24° C. a 10° C. conditioner, 54° C. initiator and 14° C. modulator. In each of FIGS. 21A-21D, the right hand plane is ground, and the left hand plane is the 2D electrode, with voltage stepping along multiple traces increasing from 30 at the bottom to 5600 volts at the top. The highest and lowest voltage traces are wide compared to the others, leading to constant voltages at the upper and lower extremes. With this arrangement, the smallest particles are found in a short arc in the lower left. The largest particles are the long arc toward the right.

Figure 22:
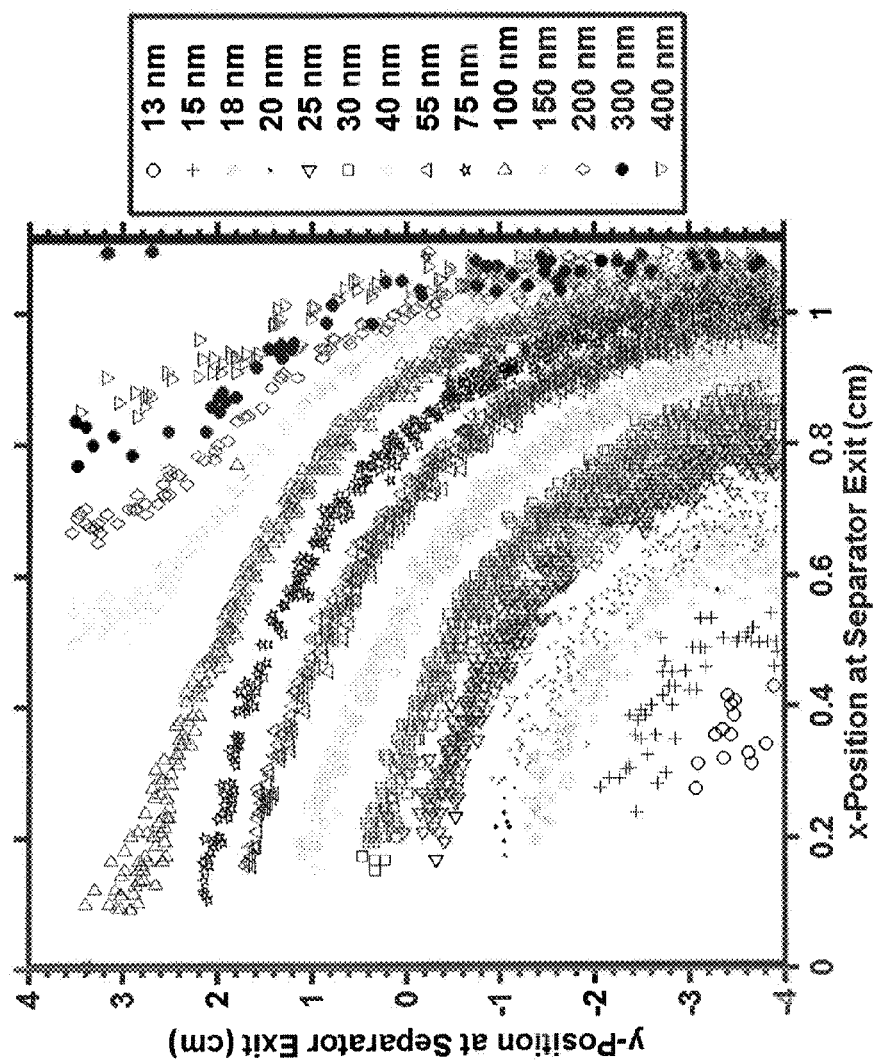
FIG. 22 shows the maximum particle concentration measurable, as determined coincidence, as a function of particle size.

FIG. 22 overlays images for particle sizes from 13 nm to 400 nm. These data were obtained for the 2D electrode operated with 30V applied to the lower electrode trace, and 5600 V applied to the upper electrode trace. Note that with this single configuration, the range of simultaneously captured particle sizes is 13-400 nm, to a factor of ~900 in mobility. Note also that the traces for each size are distinct. The sizing resolution is comparable to traditional SMPS or better.

Figure 23:
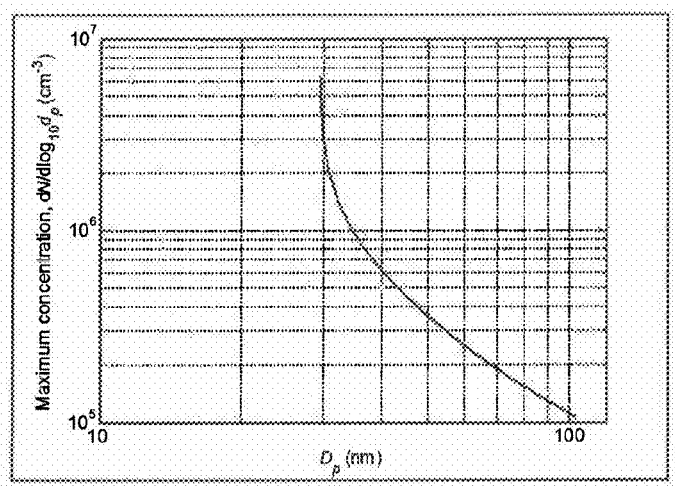
FIG. 23 shows the total number concentration measurable with the current AMI system for unimodal, lognormal distributions with the mean diameter and geometric standard deviation shown.
Figure 24:
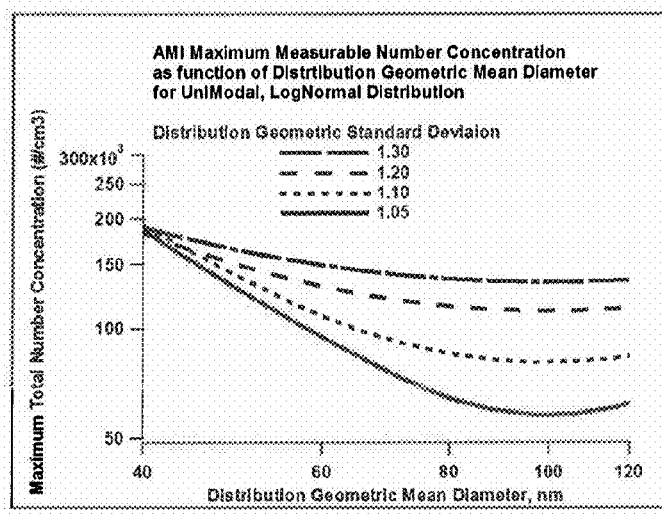
FIG. 24 is a graph of the aerosol mobility imaging maximum measurable number concentration as a function of distribution geometric mean diameter for unimodal, log-normal distribution.

For the AMI system, the upper concentration limit is governed by coincidence. Using data from the counting efficiency experiment (see, FIG. 16), which gives the maximum count density dC/dx, we calculated the upper limit of measurable particle concentration at each particle size for 10 Hz frame capture. Assuming this maximum density applies for all particle positions, and converting to dN/d log Dp for different position gives the maximum concentration limits presented in FIG. 23. Higher concentrations can be measured at the smaller sizes due to the greater spreading of the particles, and the lower charging efficiency. This function was applied to mono-modal, lognormal size distributions with geometric mean diameters between 40-110 nm, with geometric standard deviations ranging from 1.05 to 1.3. These calculations indicate that measurable concentrations extend to $5\times10^4$-$10^5$, with higher concentrations possible for aerosols with larger standard deviations (wider distributions) with geometric mean diameters below 100 nm, as presented in FIG. 24.

The lower concentration limit is governed by statistics. As is evident from the data of FIG. 20, 1 Hz data collection is possible with ambient particles at a total concentrations of $200/cm^3$. Estimates analogous to those of FIG. 24 put the lower concentration limits in the range from $100$-$1000/cm^3$. An inherent advantage of the AMI approach is that it glimpses the entire size spectrum at once. Should it require several seconds to obtain sufficient counting statistics when particle counts are very low, the measured distribution is a true average. By contrast, the scanning systems view different parts of the distributions at different times, and thus must assume a constant concentration and size distribution over the measurement interval. This assumption can lead to distorted distributions when changes are rapid. By contrast, the AMI is not subject to bias due to shifts in size or concentrations during the measurement interval. For aircraft measurements the speed gained with the AMI translates directly to spatial resolution.

Experimental evaluation of the AMI 10 shows the water condensation cell 30 provides sufficient particle growth to facilitate imaging, maintains laminar flow, efficient activates particles as small as 12 nm in diameter (with counting efficiencies of 100+−6% for all particle sizes tested, from 12 nm-100 nm). The AMI system 10 provides 1-Hz ambient size distributions, has fast time response, with a characteristic time response of 2-3, and yields size distributions which are within 15% of SMPS. It may be implemented with either a one-dimensional electrode, which provides better counting statistics but a smaller particle size range, or with a two-dimensional electrode capable of separating particles over a factor of near 1000 in mobility (e.g. from 10-500 nm).

In a further embodiment that adds a conditioner 220 ahead of the initiator 230 in the growth cell 200, it is possible to operate with low relative humidity in the sheath flow, around 20%, yet still produce supersaturated conditions, particle activation with sufficient growth to image the particles for imaging.

Certain embodiments of the present disclosure have been described above in detail. However, it is desired to emphasize that this has been for the purpose of illustrating and describing the disclosure, and should not be considered as necessarily limitative of the disclosure, it being understood that many modifications can be made by those skilled in the art while still practicing the invention, which is defined solely according to the following claims. Variants of the above-disclosed and other features and functions, or alternatives thereof may be desirably combined into many other different systems or applications. Various presently unforeseen or unanticipated alternatives, modifications, variations, or improvements therein may be subsequently made by those skilled in the art it light of the instant disclosure, those also intended to be encompassed by the following claims.

What is claimed:

1. An apparatus for measuring a size and number concentration of airborne particles, the apparatus comprising:

an elongated gap extending through the apparatus, being bounded on opposing sides by first and second substantially planar surfaces, wherein each of the planar surfaces has a width;

a sheath inlet admitting a sheath flow of fluid into the elongated gap, the sheath flow moving away from the sheath inlet in a first flow direction;

a mobility separator section downstream of the sheath inlet in the first flow direction, having an electrode forming at least part of the first planar surface of the elongated gap, and a ground plate forming at least part of the second planar surface of the elongated gap, the ground plate being opposed to the electrode;

a growth cell downstream of the mobility separator section in the first flow direction, the growth cell including a conditioning section that exposes the sheath flow to at or below ambient temperature;

an initiator section downstream of the conditioning section in the first flow direction, wherein the first and second planar surfaces of the elongated gap in the initiator section each comprises a water-saturated evaporative source, the initiator section further comprising a first heat source to expose the sheath flow to a temperature elevated above ambient; and an equilibrator section downstream of the initiator section in the first flow direction, wherein the first and second planar surfaces of the elongated gap in the equilibrator section each comprises a water-saturated evaporative source, the equilibrator section comprising:

a first heat sink to cool the planar surfaces to lower the dew point of the sheath flow to a supersaturated state; and an optical section downstream of the growth cell in the first flow direction, wherein the sheath flow is exposed to a collimated laser light plane substantially perpendicular to the direction of the sheath flow, and an observation port through which aerosol particles in the sheath flow illuminated by the laser light are observable.

2. The apparatus according to claim 1, wherein each of the water-saturated evaporative sources of the initiator section or the equilibrator section comprises a wick surface having a porosity of about 25%, a first side of the wick surface forming a part of the first or second planar surfaces of the elongated gap, the wick being saturated by water.

3. The apparatus according to claim 2, wherein each wick surface comprises art alumina bisque of about 0.25-inch thickness.

4. The apparatus according to claim 1, wherein each of the conditioning section, the initiator section, and the equilibrator section are thermally isolated from the apparatus.

5. The apparatus according to claim 4, wherein the conditioning section and the initiator section, the initiator section and the equilibrator section and the equilibrator section and the optical section are each separated by an interface, and wherein the thermal apparatus further comprises a thermally insulating separator interposed in at least one of the interfaces between the conditioning section and the initiator section, between the initiator section and the equilibrator section, or between the equilibrator section and the optical section.

6. The apparatus according to claim 4, wherein the conditioning section and the initiator section, the initiator section and the equilibrator section and the equilibrator section and the optical section are each separated by an interface, and wherein the thermal apparatus further comprises an air gap in the first and second planar surfaces interposed in at least one of the interfaces between the conditioning section and the initiator section, between the initiator section and the equilibrator section, or between the equilibrator section and the optical section.

7. The apparatus according to claim 1, wherein the first and second planar surfaces of the elongated gap in the conditioning section each comprises a water-saturated evaporative source, and wherein the equilibrator section further comprises a second heat sink to cool the sheath flow below an ambient temperature.

8. The apparatus according to claim 7, wherein each of the water-saturated evaporative sources of the conditioning section comprises a wick surface having a porosity of about 25%, a first side of the wick surface forming a part of the first or second planar surfaces of the elongated gap, the wick being saturated by water.

9. The apparatus according to claim 8, wherein the wick surface comprises an alumina bisque of about 0.25-inch thickness.

10. The apparatus according to claim 1, wherein the mobility separator section further comprises an aerosol inlet, including a slit substantially the width of either the first or second planar surface of the elongated gap, positioned upstream in the first direction with respect to the ground plate or the electrode.

11. The apparatus according to claim 1, wherein the electrode comprises a two-dimensional electrode wherein voltage potential applied to the electrode may be varied in a direction transverse to the first flow direction.

12. The apparatus according to claim 1, wherein the first heat sink comprises a thermoelectric cooler.

13. The apparatus according to claim 1, wherein the first heat source comprises a cartridge heater.

* * * * *